(12) United States Patent
Li

(10) Patent No.: US 7,235,657 B2
(45) Date of Patent: Jun. 26, 2007

(54) METHODS FOR PREPARING P2X$_7$ INHIBITORS

(75) Inventor: Zhengong Bryan Li, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/167,828

(22) Filed: Jun. 27, 2005

(65) Prior Publication Data

US 2005/0288256 A1    Dec. 29, 2005

Related U.S. Application Data

(60) Provisional application No. 60/583,851, filed on Jun. 29, 2004.

(51) Int. Cl.
*C07D 253/075* (2006.01)
*A61K 31/53* (2006.01)
*A61P 19/02* (2006.01)

(52) U.S. Cl. .................................. 544/182; 514/242
(58) Field of Classification Search ................ 544/182; 514/242

See application file for complete search history.

(56) References Cited

U.S. PATENT DOCUMENTS

| | | | |
|---|---|---|---|
| 4,318,731 A | 3/1982 | Kajioka et al. | |
| 4,594,099 A | 6/1986 | Yamada et al. | |
| 4,766,233 A | 8/1988 | Lyga | |
| 4,806,145 A | 2/1989 | Maravetz | |
| 4,906,286 A | 3/1990 | Lyga | |
| 4,906,287 A | 3/1990 | Lyga et al. | |
| 4,909,833 A | 3/1990 | Kajioka et al. | |
| 5,017,211 A | 5/1991 | Wenger et al. | |
| 5,077,409 A | 12/1991 | Wissner | |
| 5,128,351 A | 7/1992 | Wissner | |
| 5,281,614 A | 1/1994 | Ashton et al. | |
| 5,411,980 A | 5/1995 | Ashton et al. | |
| 5,686,061 A | 11/1997 | Li et al. | |
| 5,773,646 A | 6/1998 | Chandrakumar et al. | |
| 5,939,418 A | 8/1999 | Quan et al. | |
| 5,948,803 A | 9/1999 | Maeda et al. | |
| 5,961,376 A | 10/1999 | Gottschald | |
| 6,001,862 A | 12/1999 | Maeda et al. | |
| 6,020,357 A | 2/2000 | Pinto et al. | |
| 6,030,990 A | 2/2000 | Maeda et al. | |
| 6,147,101 A | 11/2000 | Maeda et al. | |
| 6,180,844 B1 | 1/2001 | Fujita et al. | |
| 6,187,797 B1 | 2/2001 | Pruitt et al. | |
| 6,201,024 B1 | 3/2001 | Baxter et al. | |
| 6,201,130 B1 | 3/2001 | Schwab et al. | |
| 6,218,376 B1 | 4/2001 | Kindon et al. | |
| 6,242,470 B1 | 6/2001 | Baxter et al. | |
| 6,258,838 B1 | 7/2001 | Baxter et al. | |
| 6,265,409 B1 | 7/2001 | Cheshire et al. | |
| 6,297,239 B1 | 10/2001 | deSolms et al. | |
| 6,303,659 B2 | 10/2001 | Baxter et al. | |
| 6,320,078 B1 | 11/2001 | Suzuki et al. | |
| 6,335,333 B1 | 1/2002 | Schwab et al. | |
| 6,451,824 B1 | 9/2002 | Thorwart et al. | |
| 6,492,355 B1 | 12/2002 | Alcaraz et al. | |
| 6,534,492 B2 | 3/2003 | Carlsen et al. | |
| 6,555,541 B1 | 4/2003 | Furber et al. | |
| 6,653,312 B1 | 11/2003 | Auvin et al. | |
| 6,720,452 B2 | 4/2004 | Alcaraz et al. | |
| 6,927,219 B2 | 8/2005 | Duplantier | |
| 6,974,812 B2 * | 12/2005 | Dombroski et al. | ........ 514/242 |
| 2003/0013704 A1 | 1/2003 | Alcaraz et al. | |
| 2003/0013721 A1 | 1/2003 | Meghani et al. | |
| 2003/0032807 A1 | 2/2003 | Andree et al. | |
| 2003/0040513 A1 | 2/2003 | Baxter et al. | |
| 2003/0186981 A1 | 10/2003 | Duplantier et al. | |
| 2004/0072876 A1 | 4/2004 | Kuroda et al. | |
| 2004/0180894 A1 | 9/2004 | Dombroski et al. | |
| 2005/0009900 A1 | 1/2005 | Dombroski et al. | |

FOREIGN PATENT DOCUMENTS

EP    0 077 938    5/1983

(Continued)

OTHER PUBLICATIONS

U.S. Appl. No. 11/168,602, filed Jun. 28, 2005, Chung et al.

(Continued)

*Primary Examiner*—Venkataraman Balasubramanian
(74) *Attorney, Agent, or Firm*—Steven R. Eck; Todd M. Crissey; Charles W. Ashbrook

(57) ABSTRACT

The present invention relates to the methods for preparing compounds of the formula I:

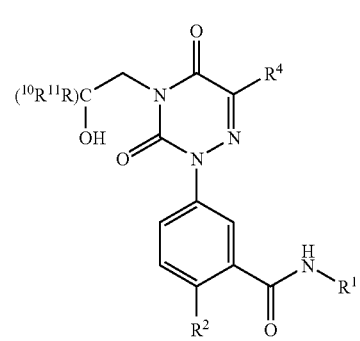

or the pharmaceutically acceptable salts thereof, wherein $R^1$, $R^2$, $R^4$, $R^{10}$, and $R^{11}$ have any of the values defined in the specification. The compounds of the present invention are useful in the treatment of diseases, including inflammatory diseases such as rheumatoid arthritis.

5 Claims, No Drawings

FOREIGN PATENT DOCUMENTS

| | | |
|---|---|---|
| EP | 0 138 527 | 4/1985 |
| EP | 0 514 339 | 11/1992 |
| EP | 0 563 384 | 10/1993 |
| EP | 0 688 773 | 12/1995 |
| WO | WO 86/00072 | 1/1986 |
| WO | WO 92/11242 | 7/1992 |
| WO | WO 93/04686 | 3/1993 |
| WO | WO 95/22532 | 8/1995 |
| WO | WO 96/01254 | 1/1996 |
| WO | WO 98/28269 | 7/1998 |
| WO | WO 99/29686 | 6/1999 |
| WO | WO 00/35864 | 6/2000 |
| WO | WO 00/71509 | 11/2000 |
| WO | WO 01/23378 | 4/2001 |
| WO | WO 01/28498 | 4/2001 |
| WO | WO 2004/058270 | 7/2004 |
| WO | WO 2004/058731 | 7/2004 |

OTHER PUBLICATIONS

U.S. Appl. No. 11/167,786, filed Jun. 27, 2005, Leonard et al.

U.S. Appl. No. 10/748,342, filed Dec. 30, 2003, Dombroski et al.

Theodoridis et al., "Synthesis and Structure-Activity Relationships of 1-Aryl-4-substituted-1,4-dihydro-5H-tetrazol-5-ones, a Novel Class of Pre- and Post-emergence Herbicides", Pestic. Sci., 1990, vol. 30, pp. 259-274.

Theodoridis et al., "Synthesis and Herbicidal Properties of Aryltriazolinones", American Chemical Society, 1992, Chapter 14, pp. 134-146.

Lyga et al., "Synthesis, Herbicidal Activity, and Action Mechanism of 2-Aryl-1,2,4-triazine-3,5-diones", American Chemical Society, 1991, Chapter 14, pp. 170-181.

Dowd et al., "P2X receptor-mediated excitation of nociceptive afferents in the normal and arthritic rat knee joint", British Journal of Pharmacology, vol. 125, No. 2, 1998, pp. 341-346.

Chang et al., "Potent and Orally Active Angiotensin II Receptor Antagonists with Equal Affinity for Human AT1 and AT2 Subtypes", J. Med. Chem., vol. 38, No. 19, 1995, pp. 3741-3758.

Chang et al., "Triazolinone Biphenylsulfonamides as Angiotensin II Receptor Antagonists with High Affinity for Both the AT1 and AT2 Subtypes", J. Med. Chem., vol. 37, No. 26, 1994, pp. 4464-4478.

Baxter et al., "Hit-to-Lead Studies: The Discovery of Potent Adamantane Amide P2X7 Receptor Antagonists", Bioorg. Med. Chem. Lett., vol. 13, No. 22, 2003, pp. 4047-4050.

Baraldi et al., "Synthesis and Biological Activity of N-Arylpiperazine-Modified Analogues of KN-62, a Potent Antagonist of the Purinergic P2X7 Receptor", J. Med. Chem., vol. 46, No. 8, 2003, pp. 1318-1329.

Chang et al., "Triazolinones as Nonpeptide Angiotensin II Antagonists. 1. Synthesis and Evaluation of Potent 2,4,5-Trisubstituted Triazolinones", J. Med. Chem., vol. 36, No. 17, 1993, pp. 2558-2568.

Bowers et al., "Pharmacological Analysis of the P2Z-Purinoceptor Present on THP-1 Cells", Drug Development Research, vol. 37, No. 3, 1996, p. 126.

PCT International Search Report, PCT/IB2005/002036.

* cited by examiner

METHODS FOR PREPARING P2X7 INHIBITORS

CROSS-REFERENCE TO RELATED APPLICATIONS

This application claims priority from U.S. Provisional Patent Application No. 60/583,851 filed Jun. 29, 2004.

BACKGROUND OF THE INVENTION

The P2X$_7$ purinergic receptor (previously known as P2Z receptor), which is a ligand-gated ion channel, is present on a variety of cell types, largely those known to be involved in inflammatory/immune process, specifically, macrophages, mast cells and lymphocytes (T and B). Activation of the P2X$_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis, and L-selectin shedding (lymphocytes). P2X$_7$ receptors are also located on antigen-presenting cells (APC), keratinocytes, salivary acinar cells (parotid cells), hepatocytes and mesangial cells.

P2X$_7$ antagonists are known in the art, such as those described in International Patent Publications WO 01/46200, WO 01/42194, WO 01/44213, WO99/29660, WO 00/61569, WO 99/29661, WO 99/29686, WO 00/71529, and WO 01/44170, as well as in WO2003042191.

Benzamides, heteroarylamides and reverse amides for uses other than inhibition of the P2X$_7$ receptor are described in various publications, such as International Patent Publications WO 97/22600, EP 138,527, WO 00/71509, WO 98/28269, WO 99/17777 and WO 01/58883.

Antagonists of the P2X$_7$ receptor are being identified for the treatment of human disease (see e.g., Alcaraz et al. (2003) *Bioorg Med Chem Lett.* 13(22):4043-4046; Baxter et al. (2003) *Bioorg Med Chem Lett.* 13(22):4047-4050). There is a need for additional compounds, compositions, and methods of preparing compounds that can inhibit the P2X$_7$ receptor for use as pharmaceutical agents.

SUMMARY OF THE INVENTION

In one aspect, the present invention provides for compounds of formula X:

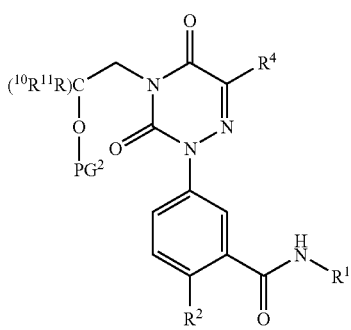

X and pharmaceutically acceptable salts thereof, wherein $R^1$ is $(C_1-C_6)$alkyl, optionally substituted by $(C_3-C_8)$cycloalkyl, phenyl, naphthyl, a 5 or 6-membered heterocycloalkyl, or a 5- or 6-membered heteroaryl, wherein each of said $(C_1-C_6)$ alkyl, $(C_3-C_8)$cycloalkyl, phenyl, naphthyl, a 5 or 6-membered heterocycloalkyl, or 5- or 6-membered heteroaryl are optionally substituted by one to three moieties independently selected from the group consisting of hydroxy, halo, —CN, $(C_1-C_6)$alkyl, —$(C_1-C_6)$alkyl-OH, $(C_1-C_6)$alkyl-NH(C=O)—, $NH_2(C=O)$—, $(C_1-C_6)$alkoxy, and $(C_3-C_8)$cycloalkyl; $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —$CF_3$, $CF_3O$—, $(C_1-C_6)$alkyl-NH—, [$(C_1-C_6)$alkyl]$_2$—N—, $(C_1-C_6)$alkyl-S—, $(C_1-C_6)$alkyl-(S=O)—, $(C_1-C_6)$alkyl-$(SO_2)$—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —$CO_2H$, $(C_1-C_6)$alkyl-O—(C=O)—, $R^5R^6N(O_2S)$—, $(C_1-C_6)$alkyl-$(O_2S)$—NH—, $(C_1-C_6)$alkyl-$O_2S$—[$(C_1-C_6)$alkyl-N]—, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $PG^2$ is a hydroxylprotecting group; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; $R^{10}$ and $R^{11}$ are independently selected from the group consisting of: $(C_1-C_6)$alkyl optionally substituted with one to three halos, hydroxy, —CN, $(C_1-C_6)$alkoxy-, (($(C_1-C_6)$alkyl)$_2$—N—, $(C_1-C_6)$ alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1-C_6)$alkyl-(C=O)O—, $(C_1-C_6)$alkyl-O(C=O)—, $(C_3-C_8)$cycloalkyl, phenyl, naphthyl, a 5 or 6-membered heterocycloalkyl, and 5- or 6-membered heteroaryl; and m is one or two. In one embodiment, the compound of formula X is 5-{4-[2-(tert-Butyl-dimethyl-silanyloxy)-3-methoxy-propyl]-3,5-dioxo-4,5-dihydro-3H-[1,2,4]triazin-2-yl}-2-chloro-N-(1-hydroxy-cycloheptylmethyl)-benzamide. In certain embodiments, $PG^2$ is selected from the group consisting of: —$SiR^{14}R^{15}R^{16}$, $C_1-C_6$alkyl, tetrahydropyranyl, and benzyl, where $R^{14}$, $R^{15}$, and $R^{16}$ are each independently selected from the group consisting of: a $(C_1-C_6)$alkyl, and a phenyl. In certain embodiments, $PG^2$ is selected from the group consisting of: trimethylsilyl, triethylsilyl, tri-isopropylsilyl, dimethylisopropylsilyl, diethylisopropylsilyl diethylisopropylsilyl, dimethylthexylsilyl, tert-butyldimethylsilyl, di-tert-butylmethylsilyl, tert-butyldiphenylsilyl, tribenzylsilyl, tri-p-xylylsilyl, triphenylsilyl, diphenylmethylsilyl, and tert-butyl(methoxy) diphenylsilyl. In certain embodiments, $R^1$ is a $(C_1-C_4)$alkyl, optionally substituted by $(C_3-C_8)$cycloalkyl; wherein said $(C_1-C_4)$alkyl or $(C_3-C_8)$cycloalkyl are optionally substituted by one to three moieties independently selected from the group consisting of hydroxy, halo, —CN, $(C_1-C_6)$alkyl, —$(C_1-C_6)$alkyl-OH, $(C_1-C_6)$alkyl-NH(C=O)—, $NH_2(C=O)$—, $(C_1-C_6)$alkoxy, and $(C_3-C_8)$cycloalkyl. In other embodiments, $R^2$ is chloro, methyl or ethyl. In certain embodiments, $R^4$ is hydrogen and $R^{10}$ and $R^{11}$ are independently selected from the group consisting of: hydrogen and $(C_1\text{-}C_6)$alkyl optionally substituted with $(C_1\text{-}C_6)$alkoxy- or —OH.

In another aspect, the present invention provides for methods of preparing compounds of the formula I:

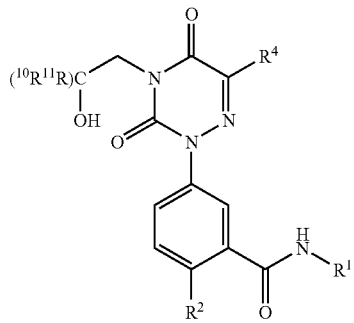

I or a pharmaceutically acceptable salt thereof, wherein $R^1$ is $(C_1\text{-}C_6)$alkyl, optionally substituted by $(C_3\text{-}C_8)$cycloalkyl, phenyl, naphthyl, a 5 or 6-membered heterocycloalkyl, or a 5- or 6-membered heteroaryl, wherein each of said $(C_1\text{-}C_6)$alkyl, $(C_3\text{-}C_8)$cycloalkyl, phenyl, naphthyl, a 5 or 6-membered heterocycloalkyl, or 5- or 6-membered heteroaryl are optionally substituted by one to three moieties independently selected from the group consisting of hydroxy, halo, —CN, $(C_1\text{-}C_6)$alkyl, —$(C_1\text{-}C_6)$alkyl-OH, $(C_1\text{-}C_6)$alkyl-NH(C=O)—, $NH_2(C=O)$—, $(C_1\text{-}C_6)$alkoxy, and $(C_3\text{-}C_8)$cycloalkyl; $R^2$ is hydrogen, halo, —CN, or $(C_1\text{-}C_6)$alkyl, wherein said $(C_1\text{-}C_6)$alkyl is optionally substituted by one to three moieties, independently selected from the group consisting of halo, hydroxy, amino, —CN, $(C_1\text{-}C_6)$alkyl, $(C_1\text{-}C_6)$alkoxy, —$CF_3$, $CF_3O$—, $(C_1\text{-}C_6)$alkyl-NH—, $[(C_1\text{-}C_6)\text{alkyl}]_2$—N—, $(C_1\text{-}C_6)$alkyl-S—, $(C_1\text{-}C_6)$alkyl-(S=O)—, $(C_1\text{-}C_6)$alkyl-$(SO_2)$—, $(C_1\text{-}C_6)$alkyl-O—(C=O)—, formyl, $(C_1\text{-}C_6)$alkyl-(C=O)—, and $(C_3\text{-}C_6)$cycloalkyl; wherein $R^4$ is independently selected from the group consisting of hydrogen, halo, hydroxy, —CN, HO—$(C_1\text{-}C_6)$alkyl, $(C_1\text{-}C_6)$alkyl optionally substituted with one to three fluoro, $(C_1\text{-}C_6)$alkoxy optionally substituted with one to three fluoro, —$CO_2H$, $(C_1\text{-}C_6)$alkyl-O—(C=O)—, $R^5R^6N(O_2S)$—, $(C_1\text{-}C_6)$alkyl-$(O_2S)$—NH—, $(C_1\text{-}C_6)$alkyl-$O_2S$—$[(C_1\text{-}C_6)$alkyl-N]—, $R^5R^6N(C=O)$—, $R^5R^6N(CH_2)_m$—, phenyl, naphthyl, $(C_3\text{-}C_8)$cycloalkyl, a 5- or 6-membered heteroaryl, a 5 or 6-membered heterocycloalkyl, phenyl-O—, naphthyl-O—, $(C_3\text{-}C_8)$cycloalkyl-O—, a 5- or 6-membered heteroaryloxy and 5 or 6-membered heterocycloalkyl-O—; $R^{10}$ and $R^{11}$ are independently selected from the group consisting of: $(C_1\text{-}C_6)$alkyl optionally substituted with one to three halos, hydroxy, —CN, $(C_1\text{-}C_6)$alkoxy-, $((C_1\text{-}C_6)\text{alkyl})_2$—N—, $(C_1\text{-}C_6)$alkyl-(C=O)—, $(C_3\text{-}C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1\text{-}C_6)$alkyl-(C=O)O—, $(C_1\text{-}C_6)$alkyl-O(C=O)—, $(C_3\text{-}C_8)$cycloalkyl, phenyl, naphthyl, a 5 or 6-membered heterocycloalkyl, and 5- or 6-membered heteroaryl; $R^5$ and $R^6$ are each independently selected from the group consisting of hydrogen, $(C_1\text{-}C_6)$alkyl, —$(C_2\text{-}C_6)$alkyl-OH, and $(C_3\text{-}C_8)$cycloalkyl, or $R^5$ and $R^6$ may optionally be taken together with the nitrogen atom to which they are attached to form a 5 or 6-membered heterocycloalkyl; and m is one or two; wherein said method comprises removing $PG^2$ from a compound of formula X

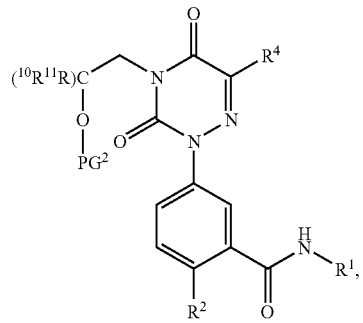

X and pharmaceutically acceptable salts thereof, wherein $PG^2$ is a hydroxyl protecting group; to form a compound of formula I. In one embodiment, the compound of formula X is 5-{4-[2-(tert-Butyl-dimethyl-silanyloxy)-3-methoxy-propyl]-3,5-dioxo-4,5-dihydro-3H-[1,2,4]triazin-2-yl}-2-chloro-N-(1-hydroxy-cycloheptylmethyl)-benzamide. In one embodiment, the compound of formula I is 2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide. In certain embodiments, $R^1$ is a $(C_1\text{-}C_4)$ alkyl, optionally substituted by $(C_3\text{-}C_8)$cycloalkyl; wherein said $(C_1\text{-}C_4)$alkyl or $(C_3\text{-}C_8)$cycloalkyl are optionally substituted by one to three moieties independently selected from the group consisting of hydroxy, halo, —CN, $(C_1\text{-}C_6)$alkyl, —$(C_1\text{-}C_6)$alkyl-OH, $(C_1\text{-}C_6)$alkyl-NH(C=O)—, $NH_2(C=O)$—, $(C_1\text{-}C_6)$alkoxy, and $(C_3\text{-}C_8)$cycloalkyl. In other embodiments, $R^2$ is chloro, methyl or ethyl. In certain embodiments, $R^4$ is hydrogen and $R^{10}$ and $R^{11}$ are independently selected from the group consisting of: hydrogen and $(C_1\text{-}C_6)$alkyl optionally substituted with $(C_1\text{-}C_6)$alkoxy- or —OH. In certain embodiments, $PG^2$ is selected from the group consisting of: —$SiR^{14}R^{15}R^{16}$, $C_1\text{-}C_6$alkyl, tetrahydropyranyl, and benzyl, where $R^{14}$, $R^{15}$, and $R^{16}$ are each independently selected from the group consisting of: a $(C_1\text{-}C_6)$alkyl, and a phenyl. In certain embodiments, $PG^2$ is selected from the group consisting of: trimethylsilyl, triethylsilyl, tri-isopropylsilyl, dimethylisopropylsilyl, diethylisopropylsilyl diethylisopropylsilyl, dimethylthexylsilyl, tert-butyldimethylsilyl, di-tert-butylmethylsilyl, tert-butyldiphenylsilyl, tribenzylsilyl, tri-p-xylylsilyl, triphenylsilyl, diphenylmethylsilyl, and tert-butyl(methoxy) diphenylsilyl. In certain embodiments, $PG^2$ is —$SiR^{14}R^{15}R^{16}$, and $PG^2$ is removed using at least one reagent selected from the group consisting of: tetrabutylammonium fluoride, $Bu_4N^+F^-$, KF, HF, $BF_3\cdot Et_2O$ pyridine-HF, triethylamine-HF, $PH_3C^+BF_4^-$, trifluroacetic acid, p-toluenesulfonic acid and HCl.

In another aspect, the present invention provides for compounds of formula IX:

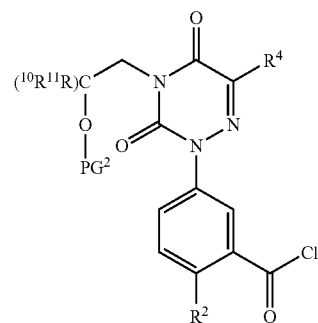

IX and pharmaceutically acceptable salts thereof, wherein $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —CF$_3$, CF$_3$O—, $(C_1-C_6)$alkyl-NH—, $[(C_1-C_6)$alkyl$]_2$—N—, $(C_1-C_6)$alkyl-S—, $(C_1-C_6)$alkyl-(S=O)—, $(C_1-C_6)$alkyl-(SO$_2$)—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —CO$_2$H, $(C_1-C_6)$alkyl-O—(C=O)—, $R^5R^6N(O_2S)$—, $(C_1-C_6)$alkyl-(O$_2$S)—NH—, $(C_1-C_6)$alkyl-O$_2$S—$[(C_1-C_6)$alkyl-N]$—, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $PG^2$ is a hydroxylprotecting group; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; $R^{10}$ and $R^{11}$ are independently selected from the group consisting of: $(C_1-C_6)$alkyl optionally substituted with one to three halos, hydroxy, —CN, $(C_1-C_6)$alkoxy-, $((C_1-C_6)$alkyl$)_2$—N—, $(C_1-C_6)$alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5 or 6-membered heteroaryl-(C=O)—, $(C_1-C_6)$alkyl-(C=O)O—, $(C_1-C_6)$alkyl-O(C=O)—, $(C_3-C_8)$cycloalkyl, phenyl, naphthyl, a 5 or 6-membered heterocycloalkyl, and 5- or 6-membered heteroaryl; and m is one or two. In certain embodiments, the compound of formula IX is 2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide. In certain embodiments, $PG^2$ is selected from the group consisting of: —SiR$^{14}$R$^{15}$R$^{16}$, $C_1$-$C_6$alkyl, tetrahydropyranyl, and benzyl, where $R^{14}$,$R^{15}$, and $R^{16}$ are each independently selected from the group consisting of: a $(C_1-C_6)$alkyl, and a phenyl. In certain embodiments, $PG^2$ is selected from the group consisting of: trimethylsilyl, triethylsilyl, tri-isopropylsilyl, dimethylisopropylsilyl, diethylisopropylsilyl diethylisopropylsilyl, dimethylthexylsilyl, tert-butyldimethylsilyl, di-tert-butylmethylsilyl, tert-butyldiphenylsilyl, tribenzylsilyl, tri-p-xylylsilyl, triphenylsilyl, diphenylmethylsilyl, and tert-butyl(methoxy)diphenylsilyl. In other embodiments, $R^2$ is chloro, methyl or ethyl. In certain embodiments, $R^4$ is hydrogen and $R^{10}$ and $R^{11}$ are independently selected from the group consisting of: hydrogen and $(C_1-C_6)$alkyl optionally substituted with $(C_1-C_6)$alkoxy- or —OH.

In another aspect, the present invention provides for compounds of formula VI:

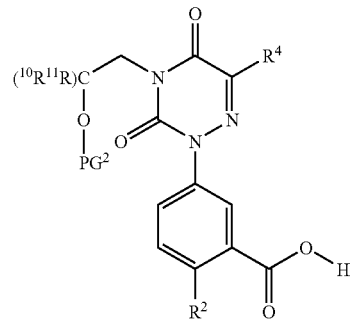

VI and pharmaceutically acceptable salts thereof, $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —CF$_3$, CF$_3$O—, $(C_1-C_6)$alkyl-NH—, $[(C_1-C_6)$alkyl$]_2$—N—, $(C_1-C_6)$alkyl-S—, $(C_1-C_6)$alkyl-(S=O)—, $(C_1-C_6)$alkyl-(SO$_2$)—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —CO$_2$H, $(C_1-C_6)$alkyl-O—(C=O)—, $R^5R^6N(O_2S)$—, $(C_1-C_6)$alkyl-(O$_2$S)—NH—, $(C_1-C_6)$alkyl-O$_2$S—$[(C_1-C_6)$alkyl-N]$—, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $PG^2$ is a hydroxyl protecting group; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; $R^{10}$ and $R^{11}$ are independently selected from the group consisting of: $(C_1-C_6)$alkyl optionally substituted with one to three halos, hydroxy, —CN, $(C_1-C_6)$alkoxy-, $((C_1-C_6)$alkyl$)_2$—N—, $(C_1-C_6)$alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5 or 6-membered heteroaryl-(C=O)—, $(C_1-C_6)$alkyl-(C=O)O—, $(C_1-C_6)$alkyl-O(C=O)—, $(C_3-C_8)$cycloalkyl, phenyl, naphthyl, a 5 or 6-membered heterocycloalkyl, and 5- or 6-membered heteroaryl; and m is one or two. In certain embodiments, the compound of formula V is 5-{4-[2-(tert-Butyl-dimethyl-silanyloxy)-3-methoxy-propyl]-3,5-dioxo-4,5-dihydro-3H-[1,2,4]triazin-2-yl}-2-chloro-benzoic acid. In certain embodiments, $PG^2$ is selected from the group consisting of: —SiR$^{14}$R$^{15}$R$^{16}$, $C_1$-$C_6$alkyl, tetrahydropyranyl, and benzyl, where $R^{14}$, $R^{15}$, and $R^{16}$ are each independently selected from the group consisting of: a $(C_1-C_6)$alkyl, and a phenyl. In certain embodiments, $PG^2$ is selected from the group consisting of: trimethylsilyl, triethylsilyl, tri-isopropylsilyl, dimethylisopropylsilyl, diethylisopropylsilyl diethylisopropylsilyl, dimethylthexylsilyl, tert-butyldimethylsilyl, di-tert-butylmethylsilyl, tert-butyldiphenylsilyl, tribenzylsilyl, tri-p-xylylsilyl, triphenylsilyl, diphenylmethylsilyl, and tert-butyl(methoxy)diphenylsilyl. In other embodiments, $R^2$ is chloro, methyl or ethyl. In certain embodiments, $R^4$ is hydrogen and $R^{10}$ and $R^{11}$ are independently selected from the group consisting of: hydrogen and $(C_1-C_6)$alkyl optionally substituted with $(C_1-C_6)$alkoxy- or —OH.

In another aspect, the present invention provides for compounds of formula V:

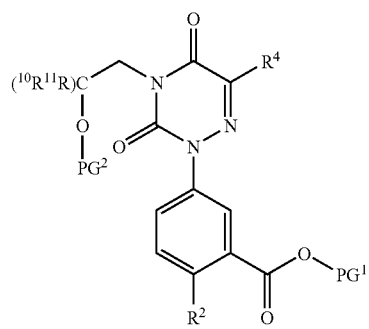

V and pharmaceutically acceptable salts thereof, wherein $PG^1$ is a carboxyl protecting group; $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —$CF_3$, $CF_3O$—, $(C_1-C_6)$alkyl-NH—, $[(C_1-C_6)$alkyl$]_2$—N—, $(C_1-C_6)$alkyl-S—, $(C_1-C_6)$alkyl-(S=O)—, $(C_1-C_6)$alkyl-$(SO_2)$—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —$CO_2H$, $(C_1-C_6)$alkyl-O—(C=O)—, $R^5R^6N(O_2S)$—, $(C_1-C_6)$alkyl-$(O_2S)$—NH—, $(C_1-C_6)$alkyl-$O_2S$—$[(C_1-C_6)$alkyl-N]$—$, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $PG^2$ is a hydroxylprotecting group; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; $R^{10}$ and $R^{11}$ are independently selected from the group consisting of: $(C_1-C_6)$alkyl optionally substituted with one to three halos, hydroxy, —CN, $(C_1-C_6)$alkoxy-, $((C_1-C_6)$alkyl$)_2$ —N—, $(C_1-C_6)$alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1-C_6)$alkyl-(C=O)O—, $(C_1-C_6)$alkyl-O(C=O)—, $(C_3-C_8)$cycloalkyl, phenyl, naphthyl, a 5 or 6-membered heterocycloalkyl, and 5- or 6-membered heteroaryl; and m is one or two. In certain embodiments, the compound of formula V is 5-{4-[2-(tert-Butyl-dimethyl-silanyloxy)-3-methoxy-propyl]-3,5-dioxo-4,5-dihydro-3H-[1,2,4]triazin-2-yl}-2-chloro-benzoic acid methyl ester. In certain embodiments, $PG^2$ is selected from the group consisting of: —$SiR^{14}R^{15}R^{16}$, $C_1-C_6$alkyl, tetrahydropyranyl, and benzyl, where $R^{14}$, $R^{15}$, and $R^{16}$ are each independently selected from the group consisting of: a $(C_1-C_6)$alkyl, and a phenyl. In certain embodiments, $PG^2$ is selected from the group consisting of: trimethylsilyl, triethylsilyl, tri-isopropylsilyl, dimethylisopropylsilyl, diethylisopropylsilyl diethylisopropylsilyl, dimethylthexylsilyl, tert-butyldimethylsilyl, di-tert-butylmethylsilyl, tert-butyldiphenylsilyl, tribenzylsilyl, tri-p-xylylsilyl, triphenylsilyl, diphenylmethylsilyl, and tert-butyl(methoxy)diphenylsilyl. In certain embodiments, $PG^1$ is selected from the group consisting of: $(C_1-C_6)$alkyl, —$SiR^{14}R^{15}R^{16}$, $C_1-C_6$alkyl, tetrahydropyranyl, and benzyl, where $R^{14}$, $R^{15}$, and $R^{16}$ are each independently selected from the group consisting of: a $(C_1-C_6)$alkyl, and a phenyl. In other embodiments, $R^2$ is chloro, methyl or ethyl. In certain embodiments, $R^4$ is hydrogen and $R^{10}$ and $R^{11}$ are independently selected from the group consisting of: hydrogen and $(C_1-C_6)$alkyl optionally substituted with $(C_1-C_6)$alkoxy- or —OH.

In another aspect, the present invention provides for compounds of formula IV:

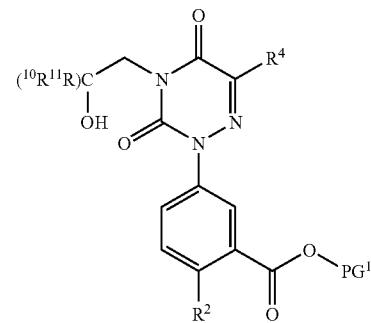

IV and pharmaceutically acceptable salts thereof, wherein $PG^1$ is a carboxyl protecting group; $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —$CF_3$, $CF_3O$—, $(C_1-C_6)$alkyl-NH—, $[(C_1-C_6)$alkyl$]_2$—N—, $(C_1-C_6)$alkyl-S—, $(C_1-C_6)$alkyl-(S=O)—, $(C_1-C_6)$alkyl-$(SO_2)$—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —$CO_2H$, $(C_1-C_6)$alkyl-O—(C=O)—, $R^5R^6N(O_2S)$—, $(C_1-C_6)$alkyl-$(O_2S)$—NH—, $(C_1-C_6)$alkyl-$O_2S$—$[(C_1-C_6)$alkyl-N]$—$, $R^5R^6N(C=O)$—, $R^1R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $R^{10}$ and $R^{11}$ are independently selected from the group consisting of: $(C_1-C_6)$alkyl optionally substituted with one to three halos, hydroxy, —CN, $(C_1-C_6)$alkoxy-, $((C_1-C_6)$alkyl$)_2$—N—, $(C_1-C_6)$alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1-C_6)$alkyl-(C=O)O—, $(C_1-C_6)$alkyl-O(C=O)—, $(C_3-C_8)$cycloalkyl, phenyl, naphthyl, a 5 or 6-membered heterocycloalkyl, and 5- or 6-membered heteroaryl; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; and m is one or two. In certain embodiments, the compound of formula IV is 2-Chloro-5-[4-(2-hydroxy-3-methoxy-propyl)-3,5-dioxo-4,5-dihydro-3H-[1,2,4]triazin-2-yl]-benzoic acid methyl ester. In certain embodiments, $PG^1$ is selected from the group consisting of: $(C_1-C_6)$alkyl, —$SiR^{14}R^{15}R^{16}$, $C_1-C_6$alkyl, tetrahydropyranyl, and benzyl, where $R^{14}$, $R^{15}$, and $R^{16}$ are each independently selected from the group consisting of: a $(C_1-C_6)$alkyl, and a phenyl. In other embodiments, $R^2$ is chloro, methyl or ethyl. In certain embodiments, $R^4$ is hydrogen and $R^{10}$ and $R^{11}$ are independently selected from the group consisting of: hydrogen and $(C_1-C_6)$alkyl optionally substituted with $(C_1-C_6)$alkoxy- or —OH.

In another aspect, the present invention provides for compounds of formula III:

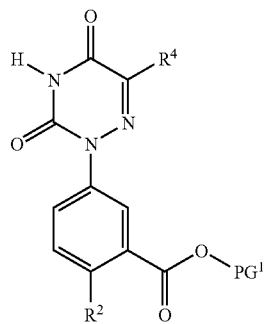

III and pharmaceutically acceptable salts thereof, wherein $PG^1$ is a carboxyl protecting group; $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —$CF_3$, $CF_3O$—, $(C_1-C_6)$alkyl-NH—, [$(C_1-C_6)$alkyl]$_2$—N—, $(C_1-C_6)$alkyl-S—, $(C_1-C_6)$alkyl-(S=O)—, $(C_1-C_6)$alkyl-($SO_2$)—, $(C_1-C_6)$alkyl-O—(C=O)—, formyl, $(C_1-C_6)$alkyl-(C=O)—, and $(C_3-C_8)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —$CO_2H$, $(C_1-C_6)$alkyl-O—(C=O)—, $R^5R^6N(O_2S)$—, $(C_1-C_6)$alkyl-($O_2S$)—NH—, $(C_1-C_6)$alkyl-$O_2S$—[$(C_1-C_6)$alkyl-N]—, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; and m is one or two. In certain embodiments, the compound of formula III is 2-Chloro-5-(3,5-dioxo-4,5-dihydro-3H-[1,2,4]triazin-2-yl)-benzoic acid methyl ester. In certain embodiments, $PG^1$ is selected from the group consisting of: $(C_1-C_6)$alkyl, —$SiR^{14}R^{15}R^{16}$, $C_1-C_6$alkyl, tetrahydropyranyl, and benzyl, where $R^{14}$, $R^{15}$ and $R^{16}$ are each independently selected from the group consisting of: a $(C_1-C_6)$alkyl, and a phenyl. In other embodiments, $R^1$ is chloro, methyl or ethyl. In certain embodiments, $R^4$ is hydrogen.

In another aspect, the present invention provides for compounds of formula Va:

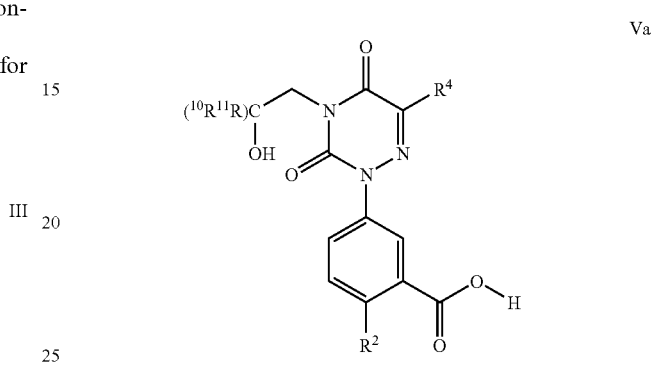

Va and pharmaceutically acceptable salts thereof, wherein $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —$CF_3$, $CF_3O$—, $(C_1-C_6)$alkyl-NH—, [$(C_1-C_6)$alkyl]$_2$—N—, $(C_1-C_6)$alkyl-S—, $(C_1-C_6)$alkyl-(S=O)—, $(C_1-C_6)$alkyl-($SO_2$)—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —$CO_2H$, $(C^1-C_6)$alkyl-O—(C=O)—, $R^5R^6N(O_2S)$—, $(C_1-C_6)$alkyl-($O_2S$)—NH—, $(C_1-C_6)$alkyl-$O_2S$—[$(C_1-C_6)$alkyl-N]—, $R^5R^6N(C=O)$—, $R^5$ $R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; $R^{10}$ and $R^{11}$ are independently selected from the group consisting of: $(C_1-C_6)$alkyl optionally substituted with one to three halos, hydroxy, —CN, $(C_1-C_6)$alkoxy-, ($(C_1-C_6)$alkyl)$_2$—N—, $(C_1-C_6)$alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1-C_6)$alkyl-(C=O)O—, $(C_1-C_6)$alkyl-O(C=O)—, $(C_3-C_8)$cycloalkyl, phenyl, naphthyl, a 5 or 6-membered heterocycloalkyl, and 5- or 6-membered heteroaryl; and m is one or two.

In another aspect, the present invention provides for methods of preparing compounds of the formula I:

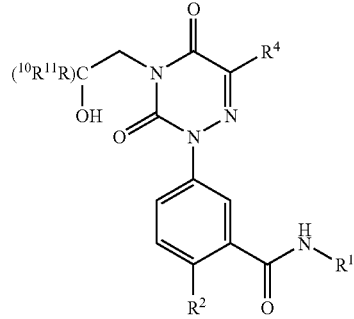

or a pharmaceutically acceptable salt thereof, wherein $R^1$ is $(C_1-C_6)$alkyl, optionally substituted by $(C_3-C_8)$cycloalkyl, phenyl, naphthyl, a 5 or 6-membered heterocycloalkyl, or a 5- or 6-membered heteroaryl, wherein each of said $(C_1-C_6)$ alkyl, $(C_3-C_8)$cycloalkyl, phenyl, naphthyl, a 5 or 6-membered heterocycloalkyl, or 5- or 6-membered heteroaryl are optionally substituted by one to three moieties independently selected from the group consisting of hydroxy, halo, —CN, $(C_1-C_6)$alkyl, —$(C_1-C_6)$alkyl-OH, $(C_1-C_6)$alkyl-NH(C=O)—, $NH_2(C=O)$—, $(C_1-C_6)$alkoxy, and $(C_3-C_8)$cycloalkyl; $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —$CF_3$, $CF_3O$—, $(C_1-C_6)$alkyl-NH—, $[(C_1-C_6)$ alkyl$]_2$—N—, $(C_1-C_6)$alkyl-S—, $(C_1-C_6)$alkyl-(S=O)—, $(C_1-C_6)$alkyl-($SO_2$)—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —$CO_2H$, $(C_1-C_6)$alkyl-O—(C=O)—, $R^5R^6N(O_2S)$—, $(C_1-C_6)$alkyl-($O_2S$)—NH—, $(C_1-C_6)$alkyl-$O_2S$—[$(C_1-C_6)$alkyl-N]—, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $R^{10}$ and $R^{11}$ are independently selected from the group consisting of: $(C_1-C_6)$alkyl optionally substituted with one to three halos, hydroxy, —CN, $(C_1-C_6)$alkoxy-, $((C_1-C_6)$ alkyl$)_2$—N—, $(C_1-C_6)$alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1-C_6)$alkyl-(C=O)O—, $(C_1-C_6)$ alkyl-O(C=O)—, $(C_3-C_8)$cycloalkyl, phenyl, naphthyl, a 5 or 6-membered heterocycloalkyl, and 5- or 6-membered heteroaryl; $R^5$ and $R^6$ are each independently selected from the group consisting of hydrogen, $(C_1-C_6)$alkyl, —$(C_2-C_6)$ alkyl-OH, and $(C_3-C_8)$cycloalkyl, or $R^5$ and $R^6$ may optionally be taken together with the nitrogen atom to which they are attached to form a 5 or 6-membered heterocycloalkyl; and m is one or two; wherein said method comprises reacting (a) a compound of formula Va:

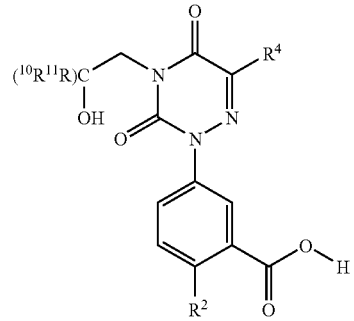

with a compound of formula $NH_2R^1$; or (b) a compound of formula IXa:

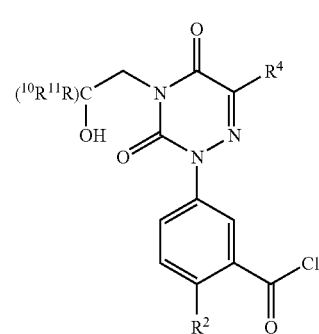

with a compound of formula $NH_2R^1$. In certain embodiments, Va is 2-Chloro-5-[4-(2$R^1$-hydroxy-3-methoxy-propyl)-3,5-dioxo-4,5-dihydro-3H-[1,2,4]triazin-2-yl]-benzoic acid). In certain embodiments, the compound of formula I is 2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide. In certain embodiments, $H^2N$—$R^1$ is 1-aminomethyl-cycloheptanol. In certain embodiments, the compound of formula IXa is 2-Chloro-5-[4-(2R-hydroxy-3-methoxy-propyl)-3,5-dioxo-4,5-dihydro-3H-[1,2,4]triazin-2-yl]-benzoyl chloride. In certain embodiments, $R^1$ is a $(C_1-C_4)$alkyl, optionally substituted by $(C_3-C_8)$cycloalkyl; wherein said $(C_1-C_4)$alkyl or $(C_3-C_8)$ cycloalkyl are optionally substituted by one to three moieties independently selected from the group consisting of hydroxy, halo, —CN, $(C_1-C_6)$alkyl, —$(C_1-C_6)$alkyl-OH, $(C_1-C_6)$alkyl-NH(C=O)—, $NH_2(C=O)$—, $(C_1-C_6)$alkoxy, and $(C_3-C_8)$cycloalkyl. In other embodiments, $R^2$ is chloro, methyl or ethyl. In certain embodiments, $R^4$ is hydrogen and $R^{10}$ and $R^{11}$ are independently selected from the group consisting of: hydrogen and $(C_1-C_6)$alkyl optionally substituted with $(C_1-C_6)$alkoxy- or —OH.

In another aspect, the present invention provides for compounds of formula IXa:

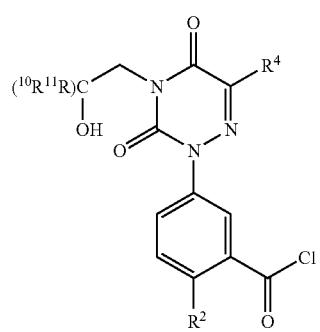

IXa and pharmaceutically acceptable salts thereof, wherein $R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —$CF_3$, $CF_3O$—, $(C_1-C_6)$alkyl-NH—, $[(C_1-C_6)$alkyl$]_2$—N—, $(C_1-C_6)$alkyl-S—, $(C_1-C_6)$alkyl-(S=O)—, $(C_1-C_6)$alkyl-$(SO_2)$—, $(C_1-C_6)$alkyl-O—(C=O)—, formyl, $(C_1-C_6)$alkyl-(C=O)—, and $(C_3-C_6)$cycloalkyl; wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —$CO_2H$, $(C^1-C_6)$alkyl-O—(C=O)—, $R^5R^6N(O_2S)$—, $(C^1-C_6)$alkyl-$(O_2S)$—NH—, $(C_1-C_6)$alkyl-$O_2S$—$[(C_1-C_6)$alkyl-N]$—, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—; $R^5$ and $R^6$ are each independently selected from the group consisting of hydrogen, $(C_1-C_6)$alkyl, —$(C_2-C_6)$alkyl-OH, and $(C_3-C_8)$cycloalkyl, or $R^5$ and $R^6$ may optionally be taken together with the nitrogen atom to which they are attached to form a 5 or 6-membered heterocycloalkyl; $R^{10}$ and $R^{11}$ are independently selected from the group consisting of: $(C_1-C_6)$alkyl optionally substituted with one to three halos, hydroxy, —CN, $(C_1-C_6)$alkoxy-, $((C_1-C_6)$alkyl$)_2$—N—, $(C_1-C_6)$alkyl-(C=O)—, $(C_3-C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1-C_6)$alkyl-(C=O)O—, $(C_1-C_6)$alkyl-O(C=O)—, $(C_3-C_8)$cycloalkyl, phenyl, naphthyl, a 5 or 6-membered heterocycloalkyl, and 5- or 6-membered heteroaryl; and m is one or two.

The compounds of this invention include all stereoisomers (e.g., cis and trans isomers) and all optical isomers (e.g., R and S enantiomers), as well as racemic, diastereomeric and other mixtures of such isomers.

The compounds, and salts of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds. One example of a tautomeric structure is when $R^3$ is a group of the formula

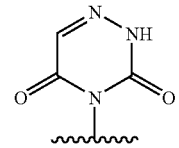

One skilled in the art will appreciate that this group can also be drawn as its tautomer

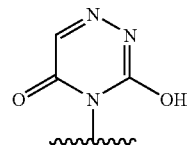

The present invention also includes atropisomers. Atropisomers refer to compounds that can be separated into rotationally restricted isomers.

The compounds of this invention may contain olefin-like double bonds. When such bonds are present, the compounds of the invention exist as cis and trans configurations and as mixtures thereof.

In another aspect, the present invention provides for methods of treating a subject suffering from a disease selected from the group consisting of rheumatoid arthritis, ankylosing spondylitis, osteoarthritis, psoriatic arthritis, psoriasis, inflammatory diseases, and autoimmune diseases, comprising: administering to a pharmaceutical composition comprising a therapeutically effective amount of a compound of formula I. In certain embodiments, the disease is rheumatoid arthritis. In certain embodiments, the disease is an "IL-1 mediated disease." As defined herein, a "IL-1 mediated disease" includes but is not limited to a disease or disorder selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic obstructive pulmonary disease, chronic pulmonary inflammatory disease, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neuro-degenerative disorders, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune disorders, Huntington's disease, diabetes, AIDS, cachexia, sepsis, septic shock, endotoxic shock, conjunctivitis shock, gram negative sepsis, toxic shock syndrome, cerebral malaria, cardiac and renal reperfusion injury, thrombosis, glomerularonephritis, graft vs. host reaction, allograft rejection, organ transplant toxicity, ulcerative colitis, and muscle degeneration.

Definitions

The term "alkyl group" or "alkyl" includes straight and branched carbon chain radicals. The term "alkylene" refers to a diradical of an unsubstituted or substituted alkane. For example, a "$C_{2-6}$ alkyl" is an alkyl group having from 2 to 6 carbon atoms. Examples of $C_2$-$C_6$ straight-chain alkyl groups include, but are not limited to, ethyl, n-propyl, n-butyl, n-pentyl, and n-hexyl. Examples of branched-chain alkyl groups include, but are not limited to, isopropyl, tert-butyl, isobutyl, etc. Examples of alkylene groups include, but are not limited to, —$CH_2$—, —$CH_2$—$CH_2$—, —$CH_2$—$CH(CH_3)$—$CH_2$—, and —$(CH_2)_{1-3}$—. Alkylene groups can be substituted with groups as set forth below for alkyl.

The term alkyl includes both "unsubstituted alkyls" and "substituted alkyls," the latter of which refers to alkyl moieties having substituents replacing a hydrogen on one or more carbons of the hydrocarbon backbone. Such substituents are independently selected from the group consisting of: halo, I, Br, Cl, F, —OH, —COOH, trifluoromethyl, —$NH_2$, —$OCF_3$, and O—$C_1$-$C_3$.

Typical substituted alkyl groups thus are 2,3-dichloropentyl, 3-hydroxy-5-carboxyhexyl, 2-aminopropyl, pentachlorobutyl, trifluoromethyl, methoxyethyl, 3-hydroxypentyl, 4-chlorobutyl, 1,2-dimethyl-propyl, and pentafluoroethyl.

"Halo" includes fluoro, chloro, bromo, and iodo.

The term "$C_3$-$C_8$cycloalkyl" refers to a cycloalkyl group containing from 3 to 8 carbons. Thus, the term "$C_3$-$C_8$cycloalkyl" encompasses monocyclic cycloalkyl groups containing from 3 to 8 carbons and bicyclic cycloalkyl groups containing 7 or 8 carbons. Examples of "$C_3$-$C_8$cycloalkyls" include, but are not limited to, cyclopropyl, cyclobutyl, cyclopentyl, cyclohexyl, cycloheptyl, and bicyclo[2.2.1]heptyl; the cycloalkyl group may optionally contain 1 or 2 double bonds (i.e., a cycloalkylenyl) including, but not limited to, cyclopentenyl, cyclohexenyl, and cycloheptenyl. A "$C_3$-$C_8$cycloalkyl" may be substituted with 1 or 2 groups independently selected from $C_1$-$C_3$alkyl (e.g., methyl) and —O-$C_1$-$C_3$alkyl (e.g., methoxy). Examples of substituted cycloalkyl groups include, but are not limited to, methyl-cyclopropyl, dimethyl-cyclohexyl, 2-methyl-cyclohexyl, 3-methyl-cyclohexyl, 3,5-dimethyl-cyclohexyl, and 4-methyl-cyclohexyl.

A "5-membered heterocycloalkyl" is a stable 5-membered, monocyclic cycloalkyl ring having from 2 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of stable 5-membered heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

A "6-membered heterocycloalkyl" is a stable 6-membered, monocyclic cycloalkyl ring having from 3 to 5 carbon atoms and from 1 to 3 heteroatoms selected from the group consisting of: 1 O; 2 O;1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of stable 6-membered heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, 1,1-dioxo-hexahydro-1$\lambda^6$-thiopyranyl, 1,1-dioxo-1$\lambda^6$-thiomorpholinyl, thiomorpholinyl, thioxanyl, and trithianyl.

The foregoing heterocycloalkyls can be C-attached or N-attached. For example, piperidinyl can be piperidin-1-yl (N-attached) or piperidin-4-yl (C-attached).

Embraced within the term "5 or 6 membered heterocycloalkyl" are 5 membered rings having one carbon-carbon or one carbon-nitrogen double bond in the ring (e.g., 2-pyrrolinyl, 3-pyrrolinyl, etc.) and 6 membered rings having one carbon-carbon or one carbon-nitrogen double bond in the ring (e.g., dihydro-2H-pyranyl, 1,2,3,4-tetrahydropyridine, 3,4-dihydro-2H-[1,4]oxazine, etc.). "5 or 6-membered heterocycloalkyls" may be substituted such as those set out above for $C_3$-$C_8$cycloalkyls, where possible.

The term "phenyl" refers to unsubstituted and substituted phenyl groups. A phenyl group may be substituted with 1 to 3 substituents independently selected from the group consisting of: $C_1$-$C_3$alkyl, —O—$C_1$-$C_3$alkyl, —$OCF_3$, halo, and a $C_5$-$C_6$ cycloalkyl.

Typical substituted phenyl groups include, but are not limited to, 3-chlorophenyl, 2,6-dibromophenyl, 2,4,6-tribromophenyl, 2,6-dichlorophenyl, 4-trifluoromethylphenyl, 3-methyl-phenyl, 4-methyl-phenyl, 3,5-dimethyl-phenyl, 3,4,5-trimethoxy-phenyl, 3,5-dimethoxy-phenyl, 3,4-dimethoxy-phenyl, 3-methoxy-phenyl, 4-methoxy-phenyl, 3,5-difluoro-phenyl, 4-chloro-phenyl, 3-trifluoromethylphenyl, 3,5-dichloro-phenyl, 2-methoxy-5-methyl-phenyl, 2-fluoro-5-methyl-phenyl, 4-chloro-2-trifluoromethyl-phenyl, and the like.

A "5-membered heteroaryl" is a stable 5-membered, monocyclic, aromatic ring radial having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of stable 5-membered heteroaryls include, but are not limited to, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl and triazolyl.

A "6-membered heteroaryl" is a stable 6-membered, monocyclic, aromatic ring radical having from 3 to 5 carbon atoms and from 1 to 3 heteroatoms selected from the group consisting of: 1 N; 2 N; and 3 N. Illustrative examples of stable 6-membered heteroaryl include pyridin-2-yl, pyridin4-yl, pyrimidin-2-yl, pyridazin4-yl, and pyrazin-2-yl.

A 5- or 6-membered heteroaryl group may be optionally substituted with 1 to 3 substituents independently selected from the group consisting of: $C_1$-$C_3$alkyl, —O—$C_1$-$C_3$alkyl, —$OCF_3$, and halo.

A "naphthyl group" refers to unsubstituted and substituted naphthyl groups. A naphthyl group may be substituted with 1 to 4 substituents independently selected from the group consisting of: $C_1$-$C_3$alkyl, —O—$C_1$-$C_3$alkyl, —$OCF_3$, halo, and a $C_5$-$C_6$ cycloalkyl.

DETAILED DESCRIPTION OF THE INVENTION

I. Process of Preparing Compounds

Compounds of formula I may be prepared as follows. $R^1$ through $R^{11}$ in the reaction schemes and discussion that follows are as defined above.

Scheme 1

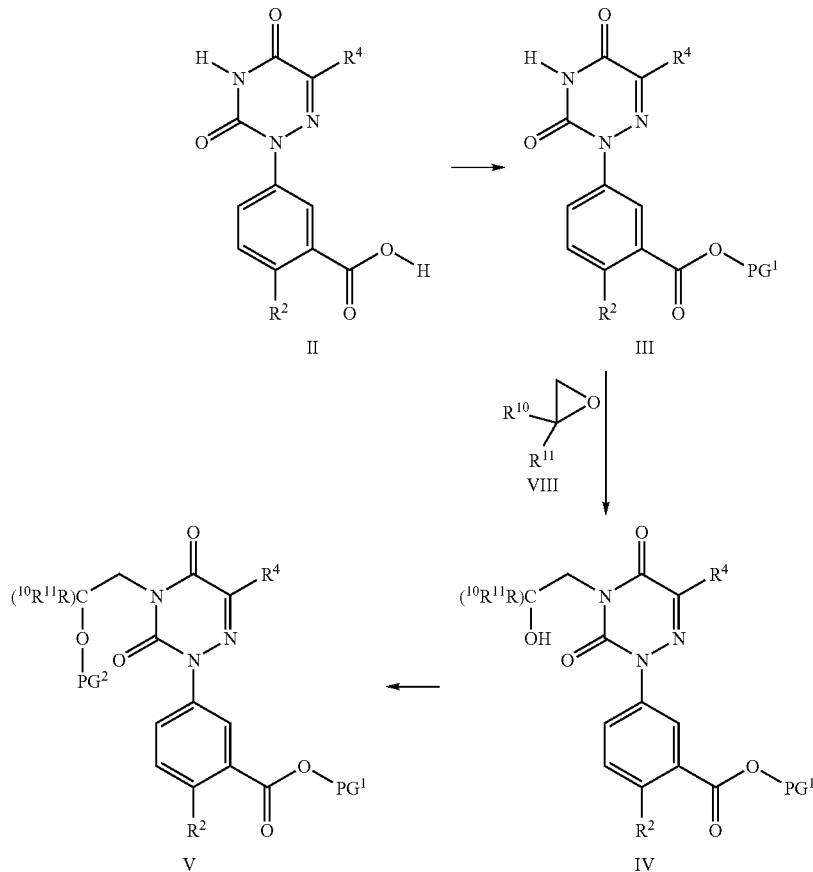

In Scheme 1, a compound of formula II (e.g., 2-Chloro-5-(3,5-dioxo-4,5-dihydro-3H-[1,2,4]triazin-2-yl)-benzoic acid) is reacted with a carboxylprotecting group reagent to form a compound of formula III. Those of skill in the art will recognize that a wide variety of protecting groups can be used as a suitable protecting group for a carboxyl group (see e.g., Greene and Wuts, *Protective Groups in Organic Synthesis*, Wiley-Interscience; 3rd edition (1999). Examples of suitable $PG^1$ carboxylprotecting groups include, but are not limited to, substituted methyl groups, phenyl, tetrahydropyranyl, tetrahydrofuranyl, cyclopentyl, cyclohexyl, 3-buten-1-yl, and —$SiR^{14}R^{15}R^{16}$, where $R^{14}$, $R^{15}$, and $R^{16}$ are each independently selected from the group consisting of: a ($C_1$-$C_6$)alkyl, and a phenyl.

Examples of substituted methyl groups suitable as $PG^1$ include 9-fluorenylmethyl, methoxymethyl, methylthiomethyl, methoxyethoxymethyl, 2-(trimethylsilyl)ethoxy-methyl, benzyloxymethyl, phenacyl, p-bromophenacyl, α methylphenacyl, p-methoxyphenacyl, carboxamidomethyl, N-phthalimidomethyl, 2,2,2-trichloroethyl, 2-haloethyl, ω-chloroalkyl, 2-(trimethylsily)ethyl, 2-methylthioethyl, 1,3-dithianyl-2-methyl, 2-(p-nitrophenylsulfenyl)-ethyl, 2-(p-toluenesulfonyl)ethyl, 2-(2'-pyridyl)ethyl, 2-(diphenylphosphino)ethyl, 1-methyl-1-phenylethyl, allyl, 4-(trimethylsily)-2-buten-1-yl, cinnamyl, α-methylcinnamyl, p-(methylmercapto)-phenyl, benzyl, triphenylmethyl, diphenylmethyl, bis(o-nitrophenyl)methyl, 9-anthrylmethyl, 2-(9,10-dioxo)anthrylmethyl, 5-dibenzo-suberyl, 1-pyrenyl-methyl,2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl) benzyl, 4-sulfobenzyl, and piperonyl.

Examples of —$SiR^{14}R^{15}R^{16}$ groups suitable as $PG^1$ include trimethylsilyl, triethylsilyl, tri-isopropylsilyl, dimethylisopropylsilyl, diethylisopropylsilyl diethylisopropylsilyl, dimethylthexylsilyl, tert-butyldimethylsilyl, di-tert-butylmethylsilyl, tert-butyldiphenylsilyl, tribenzylsilyl, tri-p-xylylsilyl, triphenylsilyl, phenyldimethylsilyl, diphenylmethylsilyl, and tert-butyl(methoxy)diphenylsilyl. The silylation step may be effected according to standard methodologies that will be known to one of ordinary skill in the art.

Compounds of formula III may be made by reacting a compound of formula II in a solvent such as dichloromethane with an acid chloride such as thionyl chloride or oxalyl chloride in the presence of a polar aprotic solvent such as ethyl acetate, methylene chloride, or dichloroethane and dimethylformamide to form the corresponding acid chloride IIa (e.g., 2-Chloro-5-(3,5-dioxo-4,5-dihydro-3H-[1,2,4]triazin-2-yl)-benzoyl chloride). The acid chloride is then reacted with a suitable carboxyl protecting group reagent (e.g., sodium methoxide) to form a compound of formula III.

In addition, II can be reacted with a base (e.g. triethylamine, alkyl-lithium, a Grignard reagent, a hydride base (e.g., sodium hydride), sodium hydroxide, NaO-tBu, KO-tBu, lithium dialkylamide, lithium diisopropylamide, lithium diethylamide, lithium bis(trimethylsilyl)amide (LiN(TMS)$_2$), sodium bis(trimethylsilyl)amide (NaN(TMS)$_2$), followed by treatment of an C$_1$-C$_6$alkyl halide to give the corresponding carboxylate ester. Alternatively, addition of an appropriate silylating agent gives the corresponding silyl carboxylate ester. The carboxylate esters may also be formed under acidic conditions (eg. Catalytic amount of concentrated H$_2$SO$_4$ in methanol, catalytic amount of p-TsOH in methanol, and acidic ion-exchange resin in methanol). Such silylating agents may comprise, for example, those silyl derivatives of the formula X—SiR$^{14}$R$^{15}$ R$^{16}$, where R$^{14}$, R$^{15}$, and R$^{16}$ are each independently selected from the group consisting of: a (C$_1$-C$_6$)alkyl, and a phenyl, and wherein X comprises an appropriate leaving group such as a halo group (e.g., chloro or bromo), cyano, imidazolyl, triflate (trifluoromethanesulfonate), and the like. Examples of silylating agents of formula X—SiR$^{14}$R$^{15}$R$^{16}$ include tert-butyldimethylsilyl chloride (TBDMSCl), triethylchlorosilane, triisopropylchlorosilane, diphenylmethylchlorosilane and tert-butyl-dimethylsilyl triflate.

Compounds of formula IV (e.g., 2-Chloro-5-[4-(2-hydroxy-3-methoxy-propyl)-3,5-dioxo-4,5-dihydro-3H-[1,2,4]triazin-2-yl]-benzoic acid methyl ester) may be prepared from compounds of formula III (e.g., 2-Chloro-5-(3,5-dioxo-4,5-dihydro-3H-[1,2,4]triazin-2-yl)-benzoic acid methyl ester) by reaction of an appropriately substituted epoxide of formula VIII (e.g., (R-(−)-glycidyl methyl ether) either neat or in the presence of a polar solvent including but not limited to dimethylformamide, dimethylsulfoxide, and tetrahydrofuran (THF). The aforesaid reaction can be performed at temperatures ranging from 0° C. to 100°C for a period of 2 to 72 hours, where the preferred conditions are dimethylforamide (DMF) at 60° C. for 24 hours.

The reaction of a compound of formula III with a compound of formula VIII to form a compound of formula IV may also be carried out in the presence of a catalytically effective amount of a Lewis acid, and a polar solvent including but not limited to N,N-dimethylformamide, N,N-dimethyl acetamide, or N-methylpyrrolidinone, dimethylsulfoxide, and tetrahydrofuran. The reaction can be performed at temperatures ranging from 0° C. to 100° C. for a period of 2 to 72 hours, where the preferred conditions are dimethylformamide at 60° C. for 24 hours. In certain embodiments, the reaction can be carried out under inert reaction conditions using an inert solvent (e.g., an anhydrous solvent) under an inert gas atmosphere (e.g., nitrogen gas). Examples of Lewis acids include compounds having the formula MXt, where M is selected from the group containing Al, As, B, Fe, Fe, Ga, Mg, Nb, Sb, Sn, Ti, and Zn. X is a halide selected from the group consisting of Cl, I, F, and Br. Those of skill in the art will recognize that t is an integer from 2 to 5 depending on the valence state of M. Examples of compounds of formula MXt include, but are not limited to: AlCl$_3$, AlI$_3$, AlF$_3$, AlBr$_3$, AsCl$_3$, AsI$_3$, AsF$_3$, AsBr$_3$, BCl$_3$, BBr$_3$, BI$_3$, BF$_3$, FeCl$_3$, FeBr$_3$, FeI$_3$, FeF$_3$, FeCl$_2$, FeBr$_2$, FeI$_2$, FeF$_2$, GaCl$_3$, GaI$_3$, GaF$_3$, GaBr$_3$, MgCl$_2$, MgI$_2$, MgF$_2$, MgBr$_2$, NbCl$_5$, SbCl$_3$, SbI$_3$, SbF$_3$, SbBr$_3$, SbCl$_5$, SbI$_5$, SbF$_5$, SbBr$_5$, SnCl$_2$, SnI$_2$, SnF2, SnBr$_2$, SnCl$_4$, SnI$_4$, SnF$_4$, SnBr$_4$, TiBr$_4$, TiCl$_2$, TiCl$_3$, TiCl$_4$, TiF$_3$, TiF$_4$, TiI$_4$, ZnCl$_2$, ZnI$_2$, ZnF$_2$, and ZnBr$_2$. In addition, Lewis acids such as Al$_2$O$_3$, BF$_3$BCl$_3$.SMe$_2$, BI$_3$.SMe$_2$, BF$_3$.SMe$_2$, BBr$_3$.SMe$_2$, BF$_3$.OEt$_2$, Et$_2$AlCl, EtAlCl$_2$, MgCl$_2$.OEt$_2$, MgI$_2$.OEt$_2$, MgF$_2$.OEt$_2$, MgBr$_2$.OEt$_2$, Et$_2$AlCl, EtAlCl$_2$, LiClO$_4$ (lithium perchlorate), Ti(O—Pr$^i$)$_4$ (titanium tetraisopropoxide), and Zn(OAc)$_2$ may be employed. In another embodiment, Cobalt (II), Copper (II), and Nickel (II) salts such as (CH$_3$CO$_2$)$_2$Co, CoBr$_2$, CoCl$_2$, CoF$_2$, CoI$_2$, Co(NO$_3$)$_2$, cobalt (II) triflate, cobalt (II) tosylate, (CH$_3$CO$_2$)$_2$ Cu, CuBr$_2$, CUCl$_2$, CuF$_2$, CuI$_2$, Cu(NO$_3$)$_2$, copper (II) triflate, copper (II) tosylate, (CH$_3$CO$_2$)$_2$Ni, NiBr$_2$, NiCl$_2$, NiF$_2$, NiI$_2$, Ni(NO$_3$)$_2$, nickel (II) triflate, and nickel (II) tosylate can be used in the reaction of VIII and II. Monoalkyl boronhalides, dialkyl boronhalides, monoaryl boronhalides, and diaryl boronhalides may be employed as Lewis acids. Rare earth metal trifluoromethanesulfonates such as Eu(OTf)$_3$, Dy(OTf)$_3$, Ho(OTf)$_3$, Er(OTf)$_3$, Lu(OTf)$_3$, Yb(OTf)$_3$, Nd(OTf)$_3$, Gd(OTf)$_3$, Lu(OTf)$_3$, La(OTf)$_3$, Pr(OTf)$_3$, Tm(OTf)$_3$, Sc(OTf)$_3$, Sm(OTf)$_3$, AgOTf, Y(OTf)$_3$, and polymer resins thereof (e.g., Scandium triflate polystyrene resin; PS-Sc(OTf)$_2$) can be used in a solution such as one part water and four to nine parts tetrahydrofuran. Furthermore, silica gels may be employed in the reaction such as silica gel (CAS 112926-00-8) used for column chromatography, preferably in the range of 80-500 mesh particle size. In certain embodiments, the Lewis Acid is a silica gel and the reaction is carried out in a solvent such as N,N-dimethylformamide, N,N-dimethyl acetamide, or N-methylpyrrolidinone, or mixtures thereof. The aforementioned Lewis acids also include heteropoly acids or their salts, zeolite-type molecular sieves, Lewis conjugate acid-type super acids, or Lewis acid (such as AlCl$_3$, BF$_3$, or XF$_5$ (X=P, As, Sb, or Bi))-treated oxide or molecular sieves, and loaded with porous inorganic carrier (such as activated C, SiO$_2$, Al$_2$O$_3$, MgO, TiO$_2$, natural or synthetic aluminosilicate-type zeolite).

The compounds of formula IV can then be reacted with a hydroxyl protecting group reagent that comprises PG$^2$ to provide a compound of formula V. The term "hydroxyl protecting group" means a functional group to protect a hydroxyl group against undesirable reactions during synthetic procedures. Examples of "hydroxyl protecting group" include, but are not limited to, silyl ethers, methyl ether, C$_1$-C$_6$alkylethers, tetrahydropyranyl and —SiR$^{14}$R$^{15}$R$^{16}$, where R$^{14}$, R$^{15}$, and R$^{16}$ are each independently selected from the group consisting of: a (C$_1$-C$_6$)alkyl, and a phenyl (See, for example, T. W. Greene, P. G. M. Wuts, Protective Groups in Organic Synthesis, New York, Wiley, 1999).

Examples of PG$^2$ include ethyl, ethyl, propyl, t-butyl, isopropyl, methoxymethyl (MOM), methylthiomethyl, t-butylthiomethyl, (phenyldimethylsilyl) methoxymethyl, benzyloxymethyl, p-ethoxybenzyloxymethyl, (4-methoxyphenoxy) methyl, guaiacolmethyl, t-butoxymethyl, 4-pentenyloxymethyl, siloxymethyl, 2-methoxyethoxymethyl, 2,2,2-trichloroethoxymethyl, bis(2-chloro-ethoxy)methyl, and 2-(trimethylsilyl)-ethoxymethyl), 1-ethoxyethyl, 1-(2,chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilyethyl, 2-(phenylselenyl)ethyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenyl-methyl, p-methoxyphenyldiphenylmethyl, di(p-methoxyphenyl)phenylmethyl, tri-(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl) methyl, 4,4',4"tris(benzoyloxyphenyl)methyl, 3-(imidazol-1-ylmethyl)bis(4', 4"-dimethoxyphenyl)-methyl, 1,1-bis(4-methoxyphenyl)-1'- pyrenylmethyl, 9-anthryl, 9-(9-phenyl) xanthenyl, 9-(9-phenyl-10-oxo) anthryl, 1,3-benzodithiolan-2-yl, and benzisothiazolyl S,S-dioxido) as well as tetrahydropyranyl, 3-bromotetrahydro-pyranyl, tetrahydrothiopyranyl, 1-methoxycyclohexyl, 4-methoxytetrahydropyranyl, 4-methoxytetrahydro-thiopyranyl, 4-methoxytetrahydrothiopyranyl S,S-dioxido, 1-[(2-chloro4-methyl)phenyl]-4-methoxypiperidin-4-yl, 1,4-dioxan-2-yl, tetrahydrofuranyl, tetrahydrothiofuranyl, and 2,3,3a,4,5,6,7,7a-octahydro-7,8,8-trimethyl4,7-ethanobenzofuran-2-yl.

Examples of —SiR$^{14}$R$^{15}$R$^{16}$ groups that may be employed as hydroxyl protecting groups include trimethyl-silyl, triethylsilyl, tri-isopropylsilyl, dimethylisopropylsilyl, diethylisopropylsilyl diethylisopropylsilyl, dimethylthexyl-silyl, tert-butyldimethylsilyl, di-tert-butylmethylsilyl, tert-butyldiphenylsilyl, tribenzylsilyl, tri-p-xylylsilyl, triphenyl-silyl, diphenylmethylsilyl, and tert-butyl(methoxy)diphenylsilyl. The silylation step may be effected according to standard methodologies that will be known to one of ordinary skill in the art.

Treatment of IV with an appropriately substituted silylating agent to form V. Such silylating agents may comprise, for example, those silyl derivatives of the formula X—SiR$^{14}$R$^{15}$R$^{16}$, where R$^{14}$, R$^{15}$, and R$^{16}$ are each independently selected from the group consisting of: a (C$_1$-C$_6$) alkyl, and a phenyl, and wherein X comprises an appropriate leaving group such as a halo group (e.g., chloro or bromo), cyano, imidazolyl, triflate (trifluoromethanesulfonate), and the like. Examples of silylating agents of formula X—SiR$^{14}$R$^{15}$R$^{16}$ include tert-butyldimethylsilyl chloride (TBDMSCI), triethylchlorosilane, triisopropylchlorosilane, diphenylmethylchlorosilane and tert-butyl-dimethylsilyl triflate.

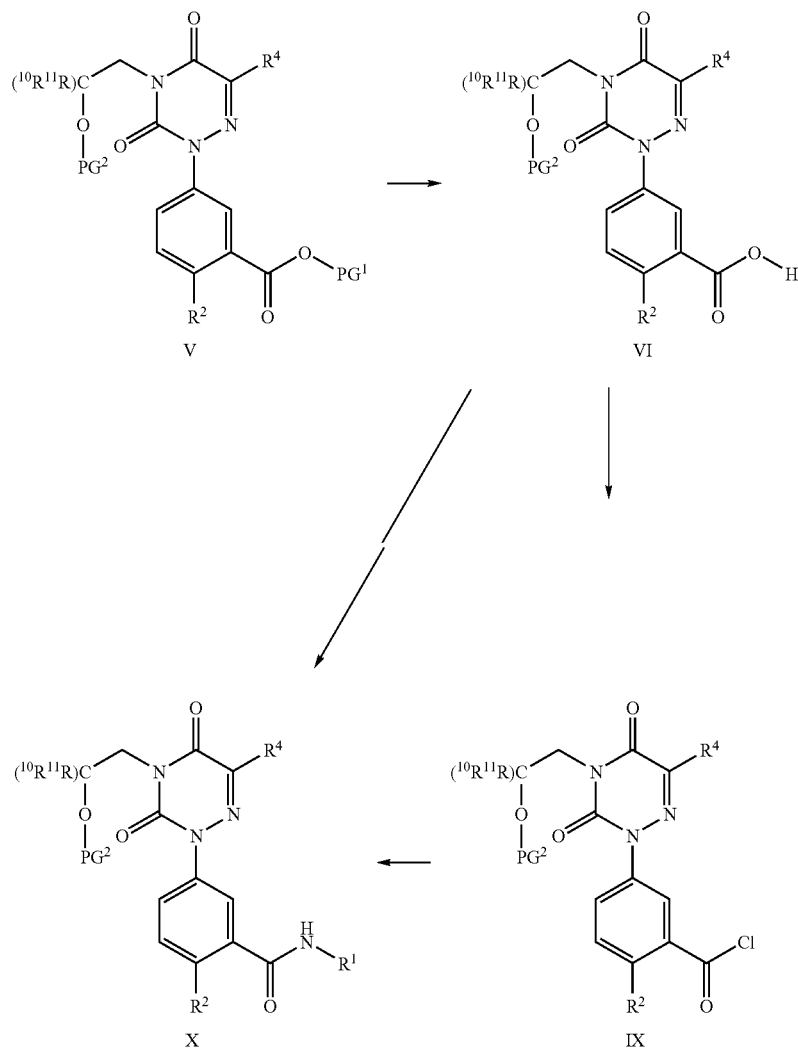

Scheme 1a

Scheme 1a refers to the preparation of compounds of formula X. The carboxyl protecting group on V (e.g., 5-{4-[2-(tert-Butyl-dimethyl-silanyloxy)-3-methoxy-propyl]-3,5-dioxo-4,5-dihydro-3H-[1,2,4]triazin-2-yl}-2-chloro-benzoic acid methyl ester) is removed to form VI (e.g., VI 5-{4-[2-(tert-Butyl-dimethyl-silanyloxy)-3-methoxy-propyl]-3,5-dioxo-4,5-dihydro-3H-[1,2,4]triazin-2-yl}-2-chloro-benzoic acid). For example protecting groups that are esters are readily hydrolyzed under basic or acidic aqueous conditions, preferably under basic conditions in a mixture of water and an organic solvent. (e.g., LiOH in water/methanol, NaOH in water/THF, $K_2CO_3$ in water/methanol), benzyl esters can be removed by hydrogenation conditions (eg. via reduction with a palladium/carbon catalyst in an alcohol solvent such as ethanol under hydrogen gas at a suitable pressure). The silyl carboxylate esters can be deprotected with a fluoride agent such as TBAF (tetrabutylammonium fluoride) (e.g., in THF), $Bu_4N^+F^-$ (e.g., in THF), KF, HF (e.g., in $CH_3CN$), $BF_3.Et_2O$ (e.g. in methanol), pyridine-HF (e.g., in THF), triethylamine-HF (e.g. in cyclohexane), $PH_3C^+BF_4^-$ (e.g. in $CH_3CN$ and $CH_2Cl_2$), trifluroacetic acid (TFA) (e.g., in water and $CH_2Cl_2$ (9:1)), and acidic conditions such as p-toluenesulfonic acid (TsOH) (e.g., in THF and water (20:1)), HCl (e.g., in ethanol), etc.

Compounds of formula X (e.g., 5-{4-[2-(tert-Butyl-dimethyl-silanyloxy)-3-methoxy-propyl]-3,5-dioxo-4,5-dihydro-3H-[1,2,4]triazin-2-yl}-2-chloro-N-(1-hydroxy-cycloheptylmethyl)-benzamide) can be prepared from compounds of formula VI by reacting with a compound of formula XIV, $H_2N-R^1$, in the presence of a coupling reagent such as 1-[3-(dimethylamino)propyl]-3-ethylcarbodiimide (EDCI), dicyclohexylcarbodiimide (DCC), 1,1'-carbonyldiimidazole (CDI) and a base such as dimethylaminopyridine (DMAP) or triethylamine in an aprotic solvent, such as methylene chloride, dimethylformamide, or dimethylsulfoxide. The aforesaid reaction may be run at a temperature from 22° C. to 60° C., for a period of 1 hour to 20 hours, preferably 22° C. for 18 hours. Compounds of formula X can also be provided by reaction of a compound of formula VI with a base such as DMAP, with N-methyl morpholine (NM) and trichlorotriazine (TCT), in dichloromethane.

Compounds of formula X may also be prepared from compounds of formula VI by reaction by reacting with a compound of formula XIV in the presence of a base including but not limited to dimethylaminopyridine (DMAP), triethylamine, aqueous sodium hydroxide or aqueous potassium hydroxide in an aprotic solvent, such as methylene chloride, ethyl acetate, dichloroethane, dimethylformamide, or dimethylsulfoxide, preferably aqueous sodium hydroxide and dichloroethane. The aforesaid reaction may be run at a temperature from 22° C. to 60° C., for a period of 1 hour to 24 hours, preferably at ambient temperature for 3 hours.

Compound VI may be reacted with a reagent capable of generating an acid chloride such as thionyl chloride or oxalyl chloride in the presence of a polar aprotic solvent such as ethyl acetate, methylene chloride, or dichloroethane at a temperature of 22° C. to 60° C., for a period of 1 hour to 24 hours (e.g., preferably oxalyl chloride in methylene chloride at ambient temperature for 16 hours) to form a compound of formula IX (e.g., 5-{4-[2-(tert-Butyl-dimethyl-silanyloxy)-3-methoxy-propyl]-3,5-dioxo-4,5-dihydro-3H-[1,2,4]triazin-2-yl}-2-chloro-benzoyl chloride). The acid chloride IX may be reacted with $NH_2R^1$ to provide a compound of X.

Scheme 2

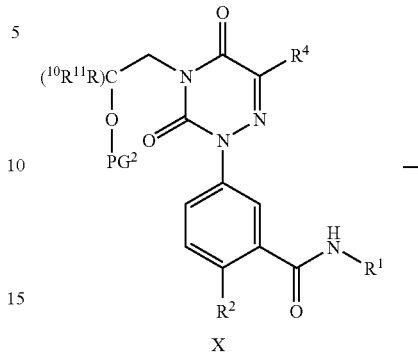

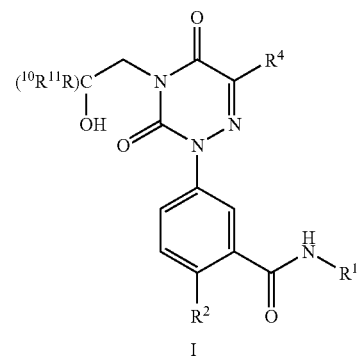

In Scheme 2, a compound of Formula X is deprotected to form a compound of Formula I. A silyl group, such as a group of $-SiR^{14}R^{15}R^{16}$, can be removed with reaction a fluoride agent such as TBAF (tetrabutylammonium fluoride) (e.g., in THF), $Bu_4N^+F^-$ (e.g., in THF), KF, HEF (e.g., in $CH_3CN$), $BF_3.Et_2O$ (e.g. in methanol), pyridine-HF (e.g., in THF), triethylamine-HF (e.g. in cyclohexane), $PH_3C^+BF_4^-$ (e.g. in $CH_3CN$ and $CH_2Cl_2$), trifluroacetic acid (TFA) (e.g., in water and $CH_2Cl_2$ (9:1)), and acidic conditions such as p-toluenesulfonic acid (TsOH) (e.g., in THF and water (20:1)), HCl ((e.g., in ethanol), etc. Methods for removing substituted methyl groups that serve as hydroxylprotecting groups as known in the art. For example, methoxymethyl ether can be hydrolyzed by HCl in methanol, $CF_3COOH$ in methylene chloride, etc. Benzyloxymethyl groups can be removed by hydrogenation using hydrogen gas and a palladium/carbon catalyst (e.g., Pd—C). Benzyl and substituted benzyl ethers can be deprotected under hydrogenation conditions with hydrogen gas and a palladium carbon catalyst (e.g., Pd—C, Pd(OH)$_2$—C, etc.). Groups such as tetrahydropyranyl can be hydrolyzed under acidic conditions (e.g. TsOH in methanol, Pyridinium p-Toluenesulfonate (PPTS), etc.).

Scheme 2a

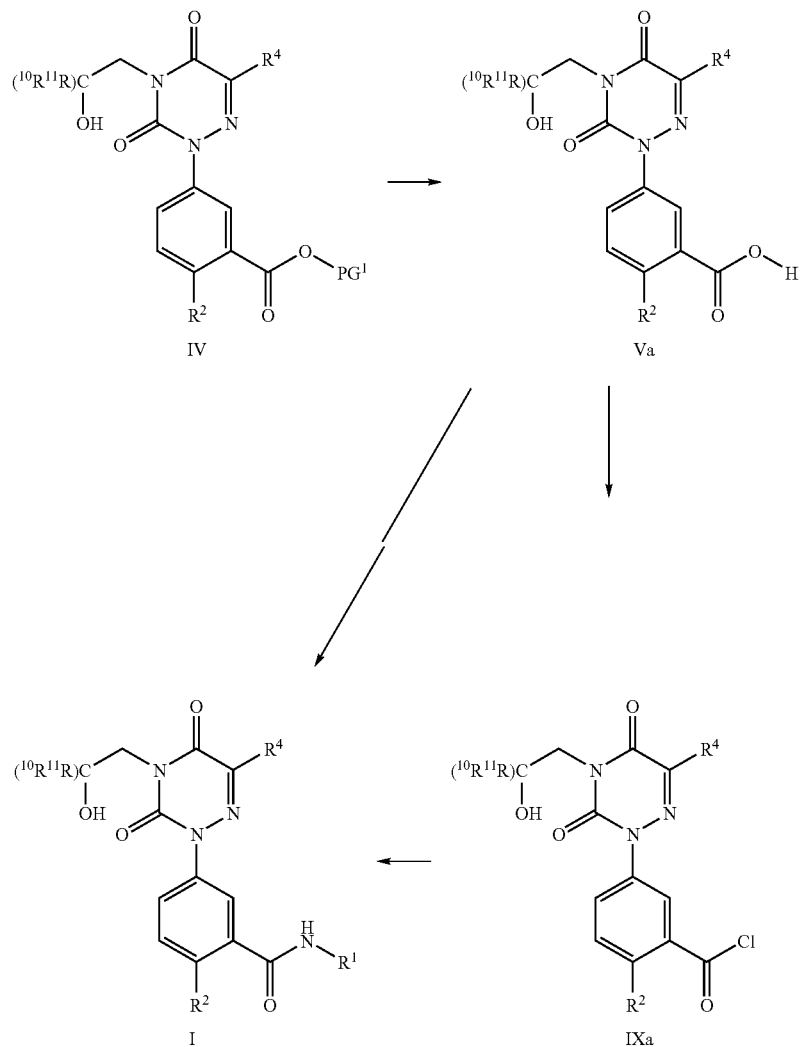

Scheme 2a refers to the preparation of compounds of formula I. The carboxylprotecting group on IV (e.g., 2-Chloro-5-[4-(2R-hydroxy-3-methoxy-propyl)-3,5-dioxo-4,5-dihydro-3H-[1,2,4]triazin-2-yl]-benzoic acid methyl ester) is removed to form Va (e.g., 2-Chloro-5-[4-(2R-hydroxy-3-methoxy-propyl)-3,5-dioxo-4,5-dihydro-3H-[1,2,4]triazin-2-yl]-benzoic acid) as described in Scheme 1a for the transformation of V to VI.

Compounds of formula I (e.g., 2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide) can be prepared from compounds of formula Va by reacting with a compound of formula XIV, $H_2N-R^1$ (e.g., 1-aminomethyl-cycloheptanol), as described in Scheme 1a for the transformation of VI to X.

Compounds of formula IXa (e.g., 2-Chloro-5-[4-(2R-hydroxy-3-methoxy-propyl)-3,5-dioxo-4,5-dihydro-3H-[1,2,4]triazin-2-yl]-benzoyl chloride) may be prepared by reacting Va with a reagent capable of generating an acid chloride such as thionyl chloride or oxalyl chloride, as described in Scheme 1a for the transformation of VI to IX.

IXa can then be reacted with a compound of formula XIV, $H_2N-R^1$ to form a compound of formula I as described in Scheme 1a for the transformation of DC to X.

Scheme 3

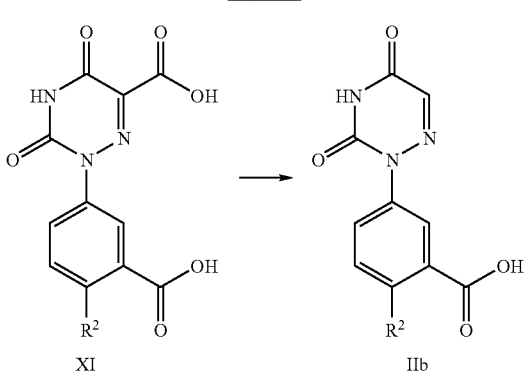

Scheme 3 refers to the preparation of compounds of formula IIb. Compounds of formula IIb may be used in place of compounds of formula II in Scheme 1. Compounds of formula I can be prepared from compounds of formula XI using decarboxylation conditions, preferably mercaptoacetic acid in water containing a base such as sodium hydroxide at a temperature from 22° C. to 160° C. for a period of 1 hour to 24 hours, preferably 100° C. for 18 hours.

Scheme 4

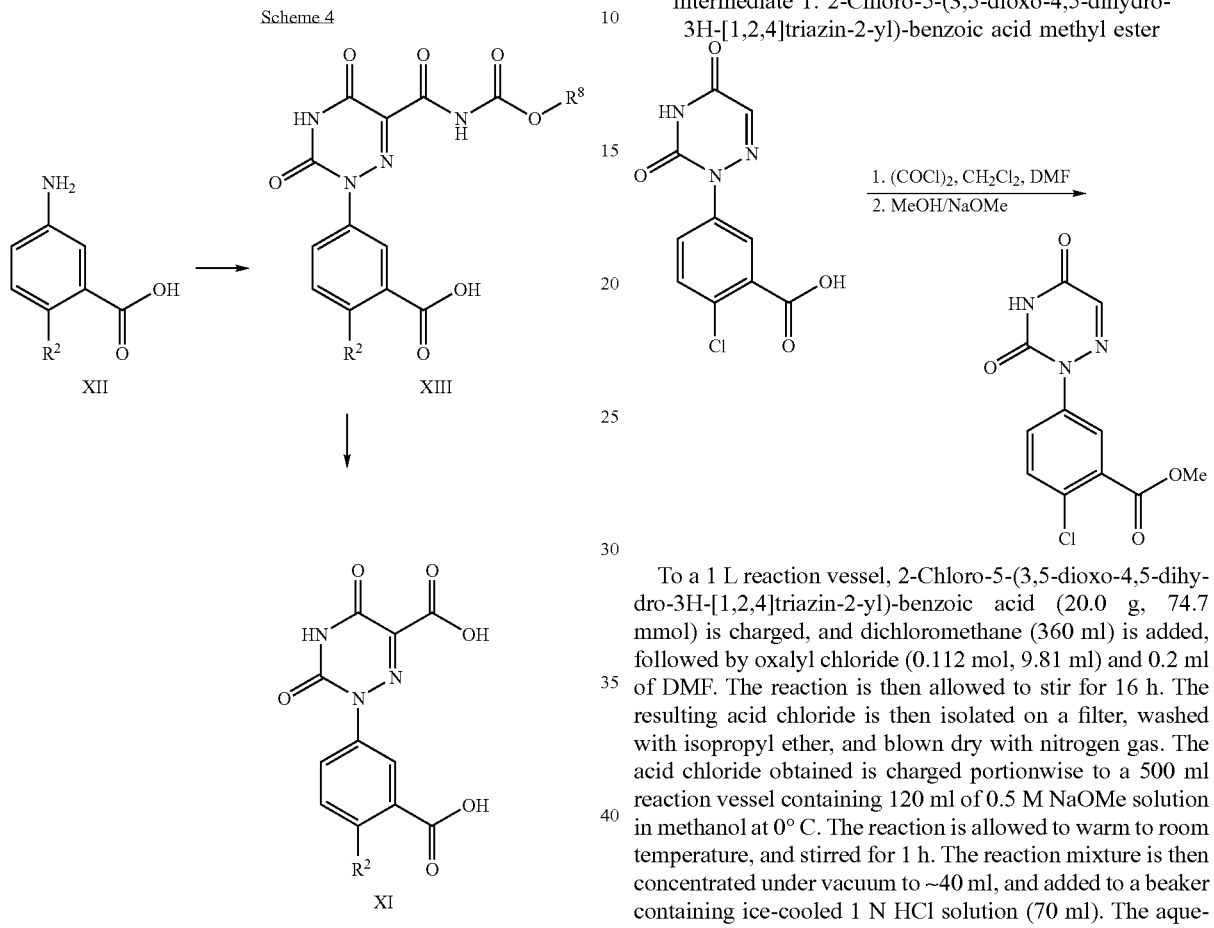

Scheme 4 refers to the preparation of compounds of formula XIII and XI. Compounds of formula XI can be converted into compounds of formula IIb by the methods described in Scheme 3.

A compound of formula XI can be prepared from a compound of formula XIII, wherein $R^8$ is a suitable ($C_1$-$C_2$)alkyl, by reaction with an acid such as 50% sulfuric acid at a temperature between 60° C. and 120° C., generally for a period between 30 minutes and 6 hours, preferably 2 hours at 120° C.

A compound of formula XIII, wherein $R^8$ is a suitable ($C_1$-$C_2$)alkyl, can be prepared from the diazonium intermediate derived from a compound of formula XII. The diazonium intermediate is prepared by reaction of a compound of formula XII with an acid such as hydrochloric acid and/or glacial acetic acid, followed by treatment with sodium nitrite in a solvent such as water at a temperature from 0° C. to 25° C., and the reaction is generally run from a period of 30 minutes to about 2 hours, preferably 10° C. for 30 minutes. A compound of formula XII is prepared by the reaction of the above diazonium intermediate with a compound of formula XVII: $R^8O(C=O)N(C=O)CH_2(C=O)N(C=O)OR^8$, under basic conditions. The reaction is typically carried out with sodium acetate as the base at a temperature from 0° C. to 120° C., preferably 10° C., then warmed to 120° C., and the reaction is generally run for a period of 1 hour to 24 hours, preferably 4 hours (Carroll et.al.; J. Med. Chem., 1983, 26, 96-100).

PROPHETIC EXAMPLE 1

Intermediate 1. 2-Chloro-5-(3,5-dioxo-4,5-dihydro-3H-[1,2,4]triazin-2-yl)-benzoic acid methyl ester

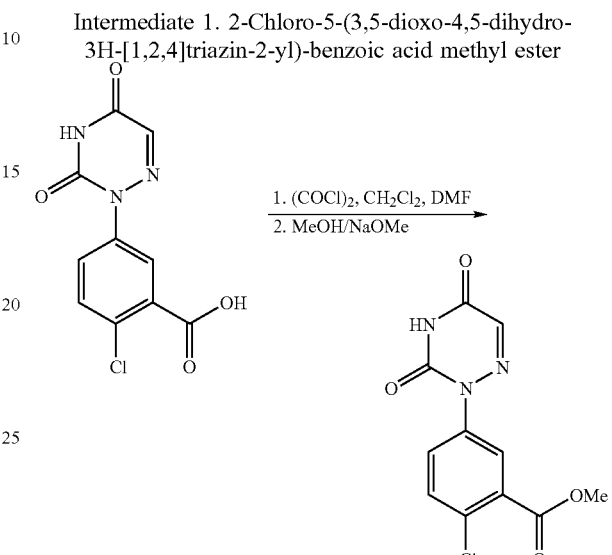

To a 1 L reaction vessel, 2-Chloro-5-(3,5-dioxo-4,5-dihydro-3H-[1,2,4]triazin-2-yl)-benzoic acid (20.0 g, 74.7 mmol) is charged, and dichloromethane (360 ml) is added, followed by oxalyl chloride (0.112 mol, 9.81 ml) and 0.2 ml of DMF. The reaction is then allowed to stir for 16 h. The resulting acid chloride is then isolated on a filter, washed with isopropyl ether, and blown dry with nitrogen gas. The acid chloride obtained is charged portionwise to a 500 ml reaction vessel containing 120 ml of 0.5 M NaOMe solution in methanol at 0° C. The reaction is allowed to warm to room temperature, and stirred for 1 h. The reaction mixture is then concentrated under vacuum to ~40 ml, and added to a beaker containing ice-cooled 1 N HCl solution (70 ml). The aqueous mixture is extracted with ethyl acetate (2×100 ml), and the combined organic phase is washed with 5% $NaHCO_3$ solution and brine solution. The organic phase is then dried over $MgSO_4$, and concentrated in vacuo to give 2-Chloro-5-(3,5-dioxo-4,5-dihydro-3H-[1,2,4]triazin-2-yl)-benzoic acid methyl ester.

Intermediate 2. 2-Chloro-5-[4-(2-hydroxy-3-methoxy-propyl)-3,5-dioxo-4,5-dihydro-3H-[1,2,4]triazin-2-yl]-benzoic acid methyl ester

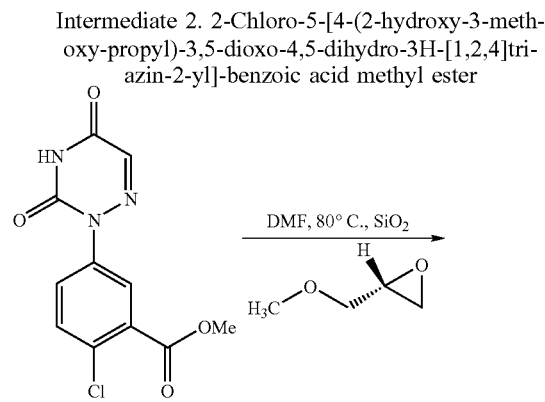

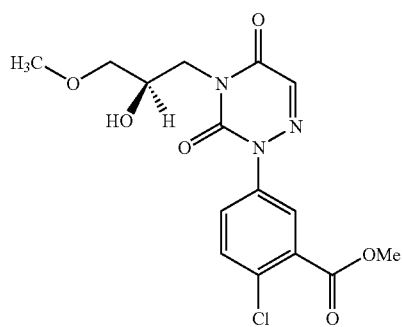

To 24 g of flash silica gel (Sigma-Aldrich Co.—catalog #288594) in a reaction vessel is added 56.8 ml of DMF. Intermediate 1 (16.0 g, 56.8 mmol) is then added, followed by R-methyl glycidyl ether (7.51 g, 85.2 mmol). The reaction is heated at 80° C. for 16 h, then cooled to 25° C. Ethyl acetate 500 ml is added to precipitate the silica gel. The silica gel is then filtered off. The ethyl acetate solution is washed with saturated 5% sodium bicarbonate solution (3×100 ml) and water (1×100 ml). The organic layers are then atmospherically concentrated in vacuum to give 2-Chloro-5-[4-(2-hydroxy-3-methoxy-propyl)-3,5-dioxo-4,5-dihydro-3H-[1,2,4]triazin-2-yl]-benzoic acid methyl ester.

Intermediate 3. 5-{4-[2-(tert-Butyl-dimethyl-silanyloxy)-3-methoxy-propyl]-3,5-dioxo-4,5-dihydro-3H-[1,2,4]triazin-2-yl}-2-chloro-benzoic acid

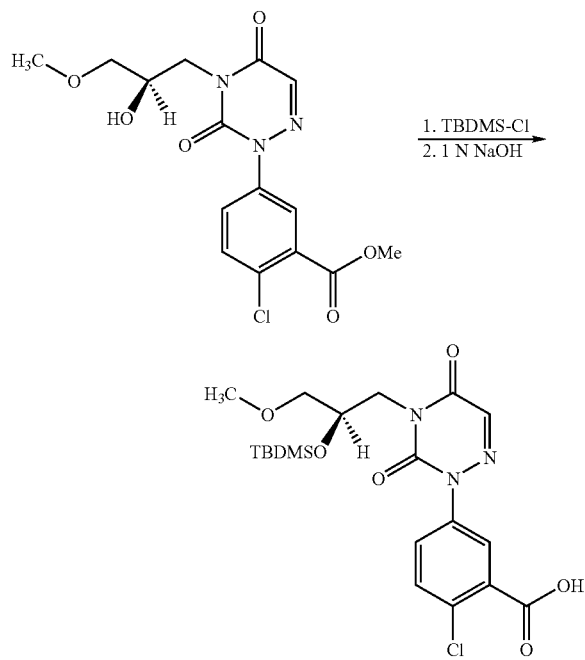

To Intermediate 2 (14.8 g, 40 mmol) in THF (200 ml) and triethylamine (44 mmol, 4.45) at 0° C., is added t-butyldimethylsilylchloride (TBDMS-Cl) (44 mmol, 6.63 g). The reaction is allowed to warm to room temperature and stirred overnight. 1 N NaOH solution (100 ml) is added, and the reaction is stirred at 40° C. for 4 h. THF is evaporated under reduced pressure, and the resulting mixture is acidified with 1 N HCl to pH<2. The mixture is extracted with ethyl acetate (2×100 ml). The organic phase is washed with brine solution, dried over MgSO$_4$, and concentrated in vacuo to give 5-{4-[2-(tert-Butyl-dimethyl-silanyloxy)-3-methoxy-propyl]-3,5-dioxo-4,5-dihydro-3H-[1,2,4]triazin-2-yl}-2-chloro-benzoic acid.

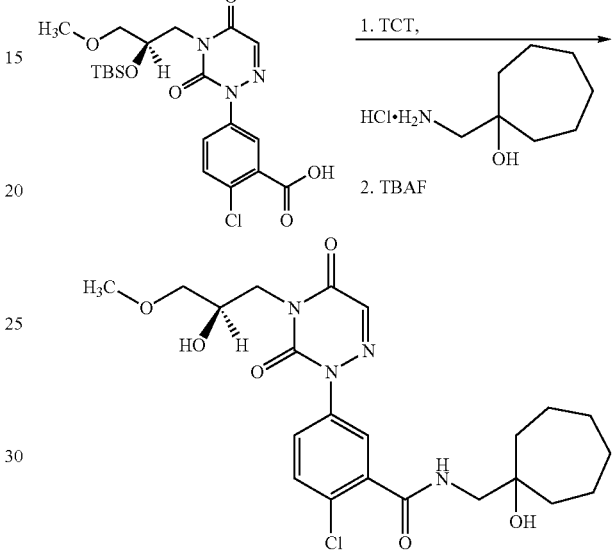

EXAMPLE 1

2-chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide Intermediate 3 (4.7 g, 10 mmol), dimethylaminopyridine (DMAP) (0.2 mmol) and N-methyl morpholine (NMM) (22 mmol) in dichloromethane (100 ml) is stirred at 0° C. Trichlorotriazine (TCT) (3.6 mmol) is added in one portion. The resulting mixture is allowed to warm to room temperature and stirred for 4 h. Then 1-aminomethyl-cycloheptanol (10 mmol) is added in one portion, the resulting mixture is stirred overnight at room temperature. 1 N TBAF (tetrabutylammonium fluoride) solution in TBIF (12 ml) is added, and the mixture is stirred at 40° C. until HPLC analysis shows sufficient deprotection of the TBDMS group. Water (100 ml) is added, and the mixture is extracted with dichloromethane. The combined organic phases are washed with water (3×100 ml), brine solution (1×50 ml), and dried over MgSO$_4$. The solution is then concentrated under vacuum, acetone (15 ml) is added to give a homogeneous solution. Then n-heptane is added until a slurry occurs, the mixture is then allowed to stir for 3 h at room temperature and filtered to give 2-chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide.

Examples of compounds which may be made using the foregoing schemes and description include those in Table I:

TABLE I

| # | STRUCTURE | NAME |
|---|-----------|------|
| 1 | 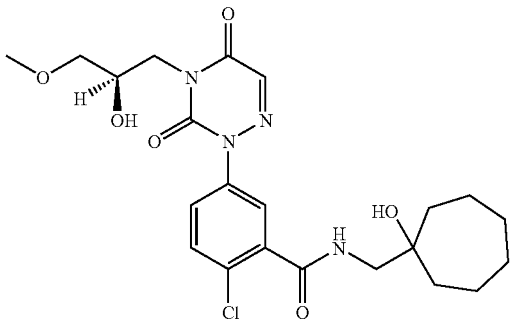 | 2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide |
| 2 | 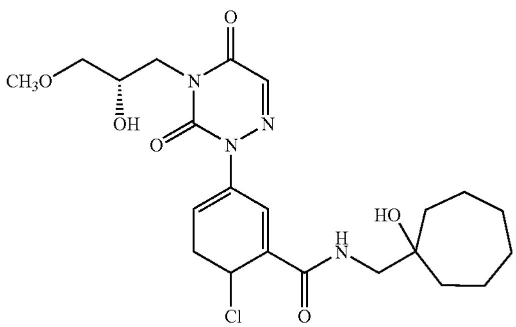 | 2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide |
| 3 | 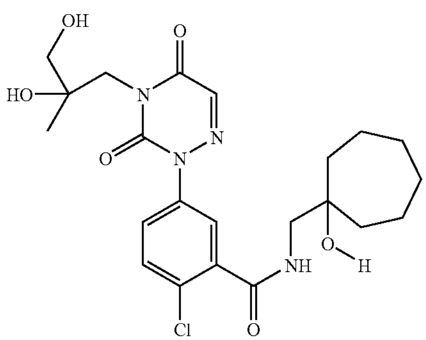 | 2-Chloro-5-[4-(2,3-dihydroxy-2-methyl-propyl)-3,5-dioxo-4,5-dihydro-3H-[1,2,4]triazin-2-yl]-N-(1-hydroxy-cycloheptylmethyl)-benzamide |
| 4 | 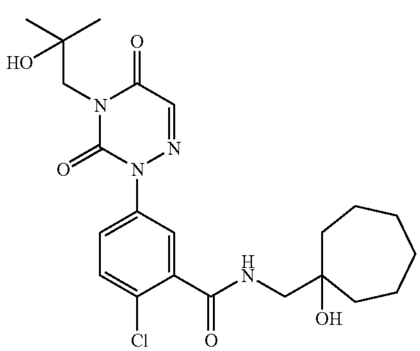 | 2-Chloro-N-(1-hydroxy-cycloheptylmethyl)-5-[4-(2-hydroxy-2-methyl-propyl)-3,5-dioxo-4,5-dihydro-3H-[1,2,4]triazin-2-yl]-benzamide |

TABLE I-continued

| # | STRUCTURE | NAME |
|---|---|---|
| 5 | 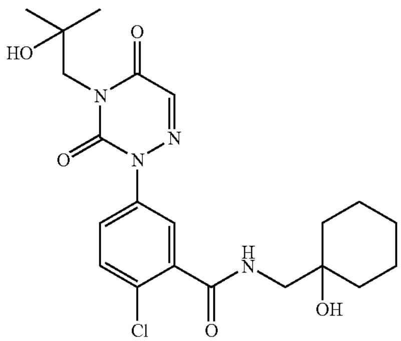 | 2-Chloro-N-(1-hydroxy-cyclohexylmethyl)-5-[4-(2-hydroxy-2-methyl-propyl)-3,5-dioxo-4,5-dihydro-3H-[1,2,4]triazin-2-yl]-benzamide |
| 6 | 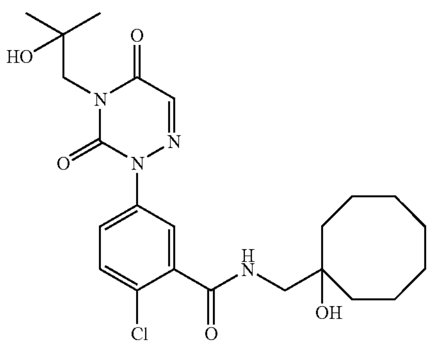 | 2-Chloro-N-(1-hydroxy cyclooctylmethyl)-5-[4-(2-hydroxy-2-methyl-propyl)-3,5-dioxo-4,5-dihydro-3H-[1,2,4]triazin-2-yl]-benzamide |
| 7 | 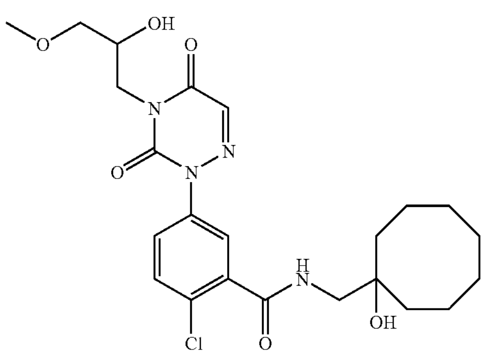 | 2-Chloro-N-(1-hydroxy-cyclooctylmethyl)-5-[4-(2-hydroxy-3-methoxy-propyl)-3,5-dioxo-4,5-dihydro-3H-[1,2,4]triazin-2-yl]-benzamide |
| 8 | 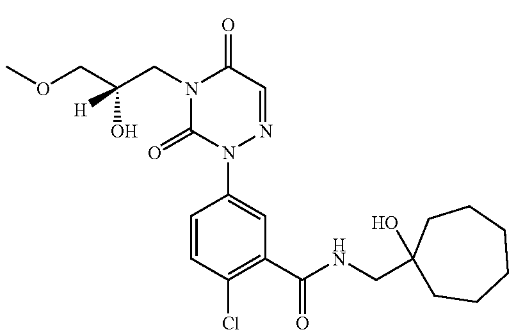 | 2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide |

TABLE I-continued

| # | STRUCTURE | NAME |
|---|-----------|------|
| 9 | 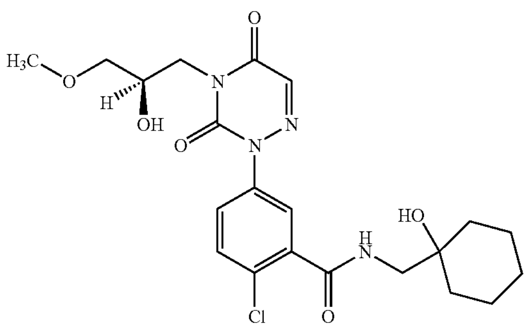 | 2-Chloro-N-(1-hydroxy-cyclohexylmethyl)-5-[4-(2-hydroxy-3-methoxy-propyl)-3,5-dioxo-4,5-dihydro-3H-[1,2,4]triazin-2-yl]-benzamide |
| 10 | 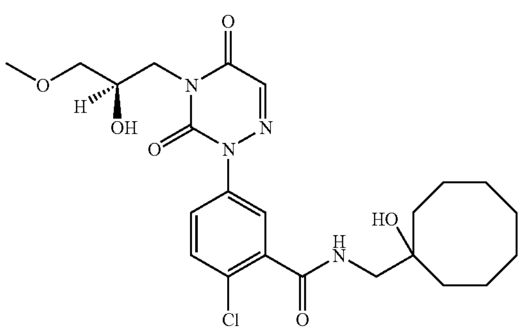 | 2-Chloro-N-(1-hydroxy-cyclooctylmethyl)-5-[4-(2-hydroxy-3-methoxy-propyl)-3,5-dioxo-4,5-dihydro-3H-[1,2,4]triazin-2-yl]-benzamide |
| 11 | 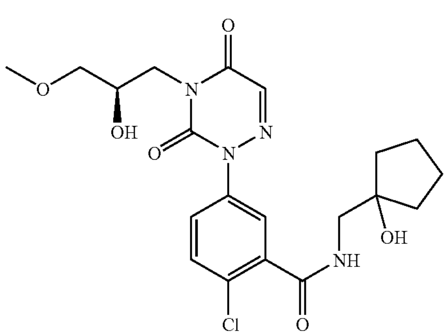 | 2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide |
| 12 | 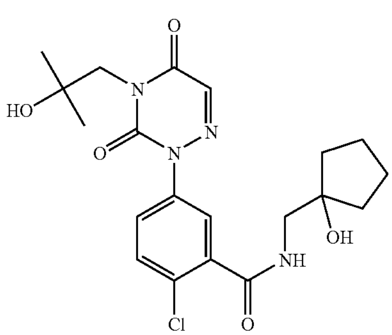 | 2-Chloro-N-(1-hydroxy-cyclopentylmethyl)-5-[4-(2-hydroxy-2-methyl-propyl)-3,5-dioxo-4,5-dihydro-3H-[1,2,4]triazin-2-yl]-benzamide |

TABLE I-continued

| # | STRUCTURE | NAME |
|---|-----------|------|
| 13 | 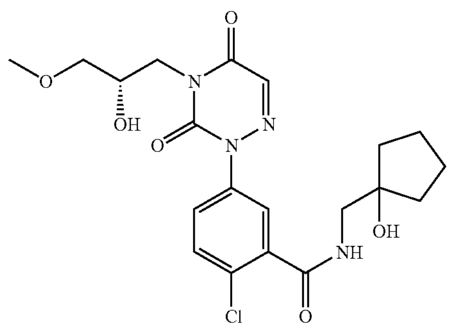 | 2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide |
| 14 | 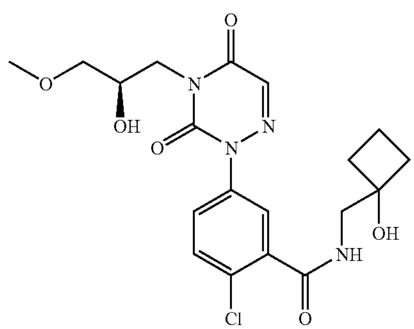 | 2-Chloro-N-(1-hydroxy-cyclobutylmethyl)-5-[4-(2-hydroxy-3-methoxy-propyl)-3,5-dioxo-4,5-dihydro-3H-[1,2,4]triazin-2-yl]-benzamide |
| 15 | 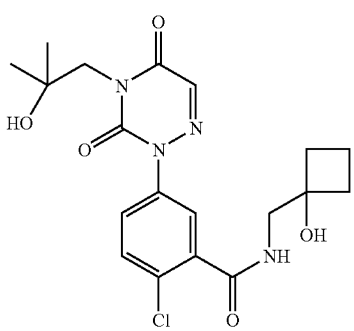 | 2-Chloro-N-(1-hydroxy-cyclobutylmethyl)-5-[4-(2-hydroxy-2-methyl-propyl)-3,5-dioxo-4,5-dihydro-3H-[1,2,4]triazin-2-yl]-benzamide |
| 16 | 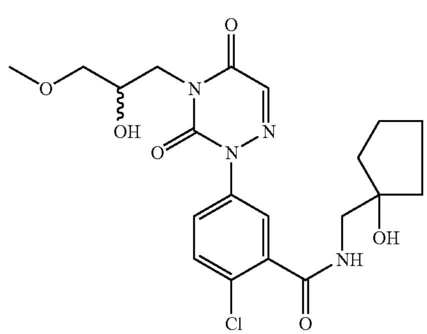 | 2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide |

TABLE I-continued

| # | STRUCTURE | NAME |
|---|-----------|------|
| 17 | 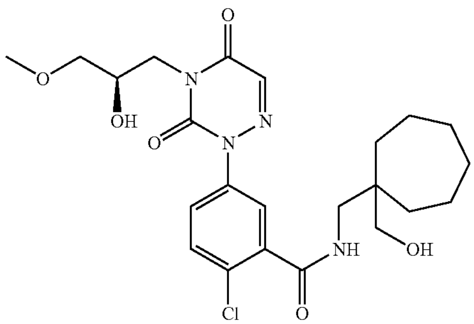 | 2-Chloro-5-[4-(2-hydroxy-3-methoxy-propyl)-3,5-dioxo-4,5-dihydro-3H-[1,2,4]triazin-2-yl]-N-(1-hydroxymethyl-cycloheptylmethyl)-benzamide |
| 18 | 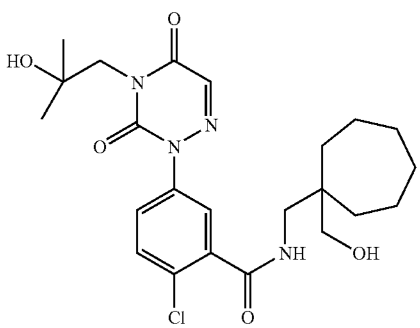 | 2-Chloro-N-(1-hydroxymethyl-cycloheptylmethyl)-5-[4-(2-hydroxy-2-methyl-propyl)-3,5-dioxo-4,5-dihydro-3H-[1,2,4]triazin-2-yl]-benzamide |
| 19 | 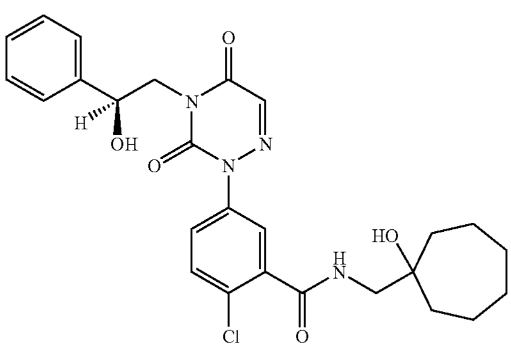 | 2-Chloro-N-(1-hydroxy-cycloheptylmethyl)-5-[4-(2-hydroxy-2-phenyl-ethyl)-3,5-dioxo-4,5-dihydro-3H-[1,2,4]triazin-2-yl]-benzamide |
| 20 | 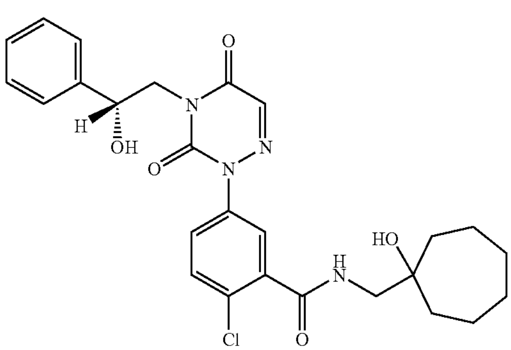 | 2-Chloro-N-(1-hydroxy cycloheptylmethyl)-5-[4-(2-hydroxy-2-phenyl-ethyl)-3,5-dioxo-4,5-dihydro-3H-[1,2,4]triazin-2-yl]-benzamide |

TABLE I-continued

| # | STRUCTURE | NAME |
|---|---|---|
| 21 | 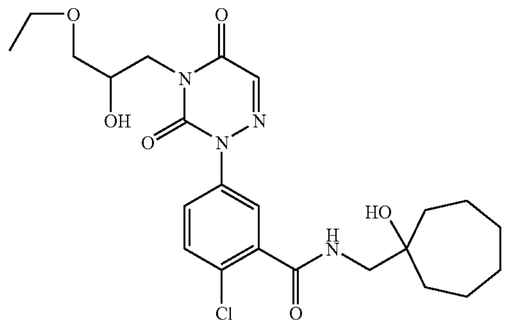 | 2-Chloro-5-[4-(3-ethoxy-2-hydroxy-propyl)-3,5-dioxo-4,5-dihydro-3H-[1,2,4]triazin-2-yl]-N-(1-hydroxy-cycloheptylmethyl)-benzamide |
| 22 | 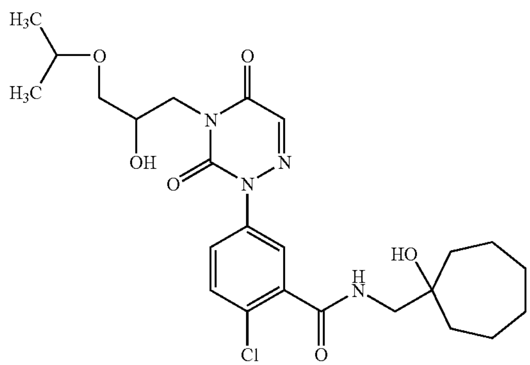 | 2-Chloro-N-(1-hydroxy-cycloheptylmethyl)-5-[4-(2-hydroxy-3-isopropoxy-propyl)-3,5-dioxo-4,5-dihydro-3H-[1,2,4]triazin-2-yl]-benzamide |
| 23 | 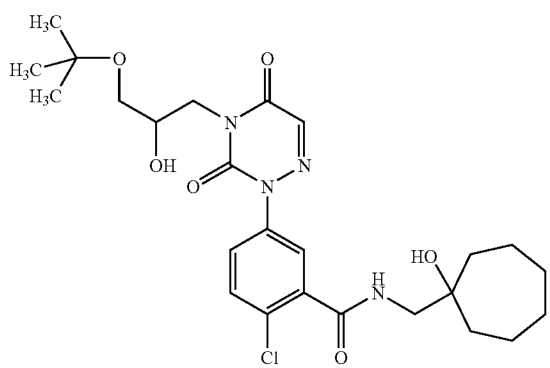 | 5-[4-(3-tert-Butoxy-2-hydroxy-propyl)-3,5-dioxo-4,5-dihydro-3H-[1,2,4]triazin-2-yl]-2-chloro-N-(1-hydroxy-cycloheptylmethyl)-benzamide |
| 24 | 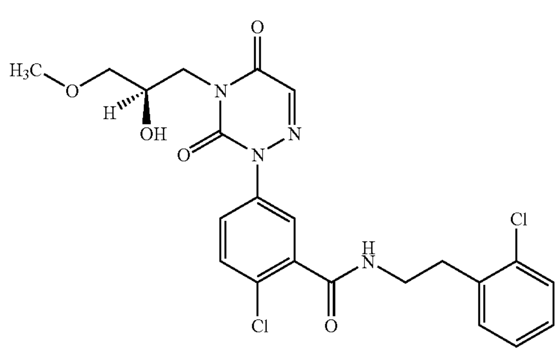 | 2-Chloro-N-[2-(2-chloro-phenyl)-ethyl]-5-[4-(2-hydroxy-3-methoxy-propyl)-3,5-dioxo-4,5-dihydro-3H-[1,2,4]triazin-2-yl]-benzamide |

TABLE I-continued

| # | STRUCTURE | NAME |
|---|---|---|
| 25 | 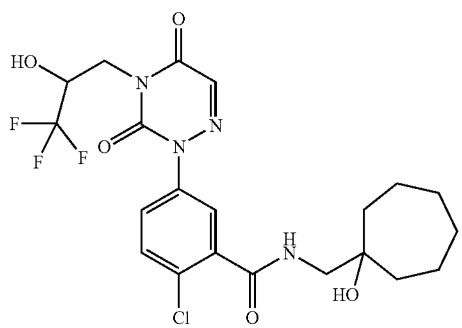 | 2-Chloro-5-[3,5-dioxo-4-(3,3,3-trifluoro-2-hydroxy-propyl)-4,5-dihydro-3H-[1,2,4]triazin-2-yl]-N-(1-hydroxy-cycloheptylmethyl)-benzamide |
| 26 | 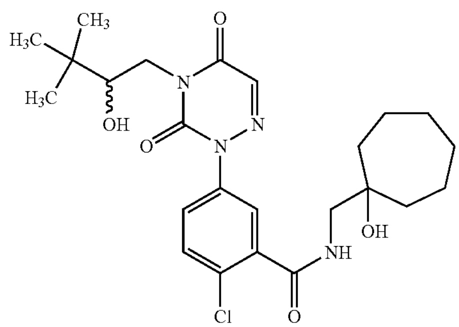 | 2-Chloro-N-(1-hydroxy-cycloheptylmethyl)-5-[4-(2-hydroxy-3,3-dimethyl-butyl)-3,5-dioxo-4,5-dihydro-3H-[1,2,4]triazin-2-yl]-benzamide |
| 27 | 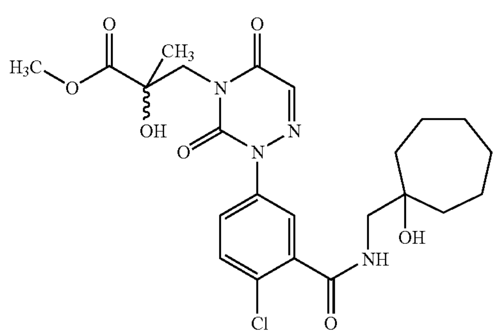 | 3-(2-{4-Chloro-3-[(1-hydroxy-cycloheptylmethyl)-carbamoyl]-phenyl}-3,5-dioxo-2,5-dihydro-3H-[1,2,4]triazin-4-yl)-2-hydroxy-2-methyl-propionic acid methyl ester |
| 28 | 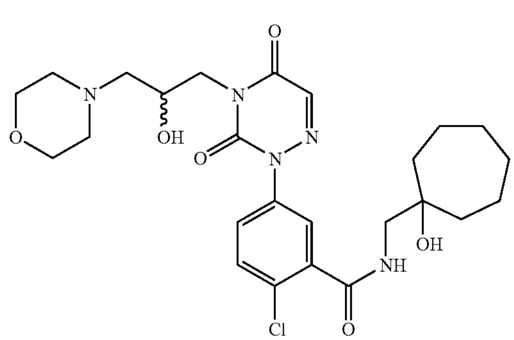 | 2-Chloro-N-(1-hydroxy-cycloheptylmethyl)-5-[4-(2-hydroxy-3-morpholin-4-yl-propyl)-3,5-dioxo-4,5-dihydro-3H-[1,2,4]triazin-2-yl]-benzamide |

TABLE I-continued

| # | STRUCTURE | NAME |
|---|---|---|
| 29 | 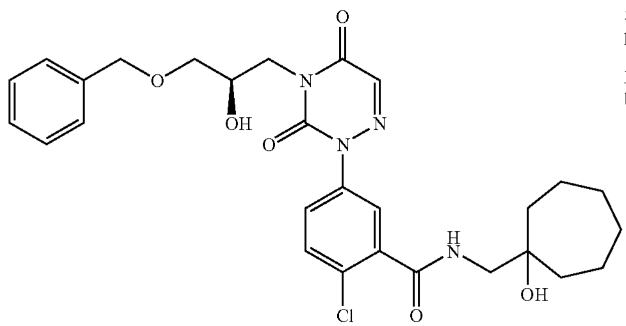 | 5-[4-(3-Benzyloxy-2-hydroxy-propyl)-3,5-dioxo-4,5-dihydro-3H-[1,2,4]triazin-2-yl]-2-chloro-N-(1-hydroxy-cycloheptylmethyl)benzamide |
| 30 | 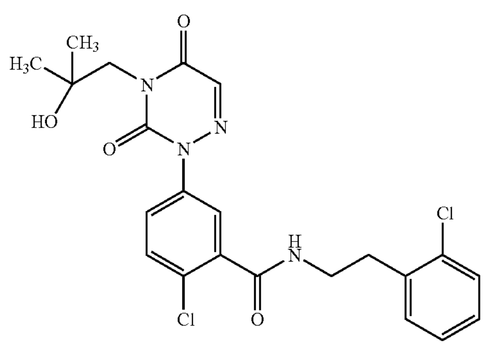 | 2-Chloro-N-[2-(2-chloro-phenyl)-ethyl]-5-[4-(2-hydroxy-2-methyl-propyl)-3,5-dioxo-4,5-dihydro-3H-[1,2,4]triazin-2-yl]-benzamide |
| 31 | 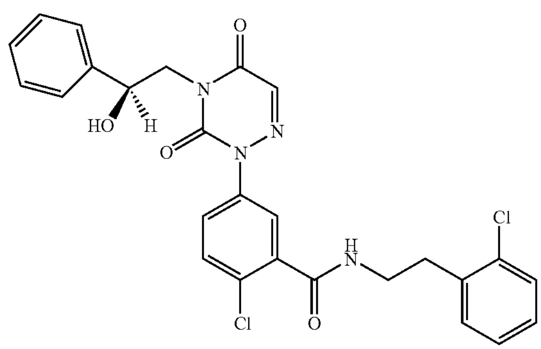 | 2-Chloro-N-[2-(2-chloro-phenyl)-ethyl]-5-[4-(2-hydroxy-2-phenyl-ethyl)-3,5-dioxo-4,5-dihydro-3H-[1,2,4]triazin-2-yl]-benzamide |
| 32 | 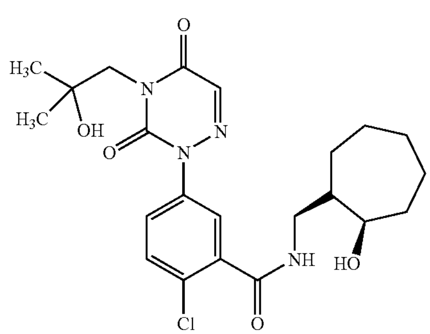 | 2-Chloro-N-(2-hydroxy-cycloheptylmethyl)-5-[4-(2-hydroxy-2-methyl-propyl)-3,5-dioxo-4,5-dihydro-3H-[1,2,4]triazin-2-yl]-benzamide |

TABLE I-continued

| # | STRUCTURE | NAME |
|---|-----------|------|
| 33 | 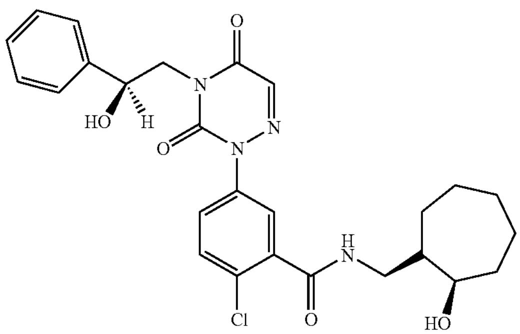 | 2-Chloro-N-(2-hydroxy-cycloheptylmethyl)-5-[4-(2-hydroxy-2-phenyl-ethyl)-3,5-dioxo-4,5-dihydro-3H-[1,2,4]triazin-2-yl]-benzamide |
| 34 | 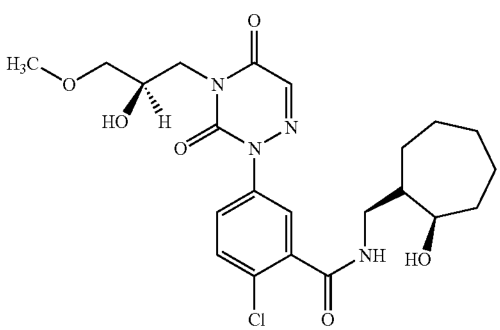 | 2-Chloro-N-(2-hydroxy-cycloheptylmethyl)-5-[4-(2-hydroxy-3-methoxy-propyl)-3,5-dioxo-4,5-dihydro-3H-[1,2,4]triazin-2-yl]-benzamide |
| 35 | 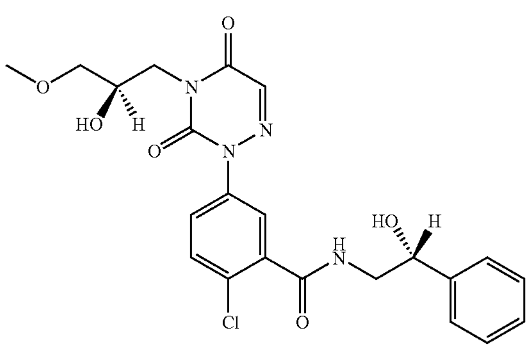 | 2-Chloro-5-[4-(2-hydroxy-3-methoxy-propyl)-3,5-dioxo-4,5-dihydro-3H-[1,2,4]triazin-2-yl]-N-(2-hydroxy-2-phenyl-ethyl)-benzamide |
| 36 | 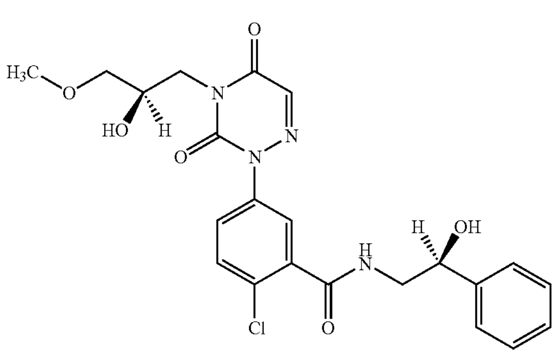 | 2-Chloro-5-[4-(2-hydroxy-3-methoxy-propyl)-3,5-dioxo-4,5-dihydro-3H-[1,2,4]triazin-2-yl]-N-(2-hydroxy-2-phenyl-ethyl)-benzamide |

TABLE I-continued

| # | STRUCTURE | NAME |
|---|-----------|------|
| 37 | 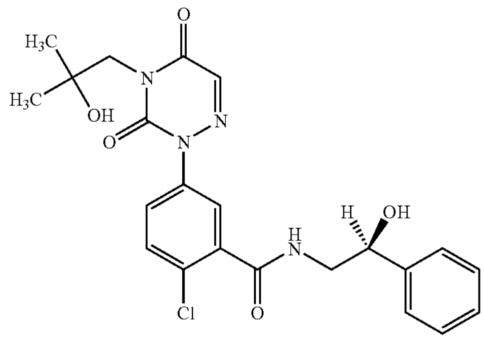 | 2-Chloro-5-[4-(2-hydroxy-2-methyl-propyl)-3,5-dioxo-4,5-dihydro-3H-[1,2,4]triazin-2-yl]-N-(2-hydroxy-2-phenyl-ethyl)-benzamide |
| 38 | 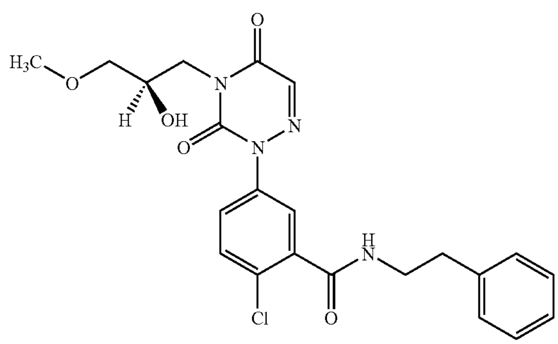 | 2-Chloro-5-[4-(2-hydroxy-3-methoxy-propyl)-3,5-dioxo-4,5-dihydro-3H-[1,2,4]triazin-2-yl]-N-phenethyl-benzamide |
| 39 | 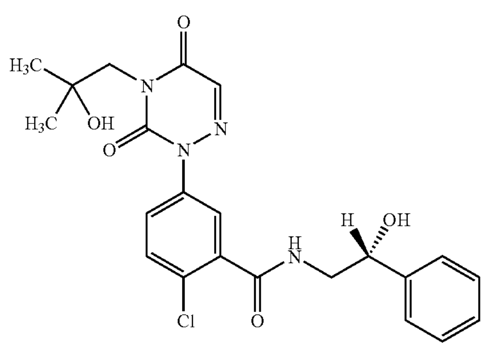 | 2-Chloro-5-[4-(2-hydroxy-2-methyl-propyl)-3,5-dioxo-4,5-dihydro-3H-[1,2,4]triazin-2-yl]-N-(2-hydroxy-2-phenyl-ethyl)-benzamide |
| 40 | 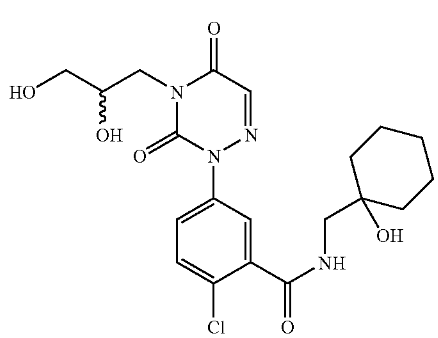 | 2-Chloro-5-[4-(2,3-dihydroxy-propyl)-3,5-dioxo-4,5-dihydro-3H-[1,2,4]triazin-2-yl]-N-(1-hydroxy-cyclohexylmethyl)-benzamide |

TABLE I-continued

| # | STRUCTURE | NAME |
|---|---|---|
| 41 | 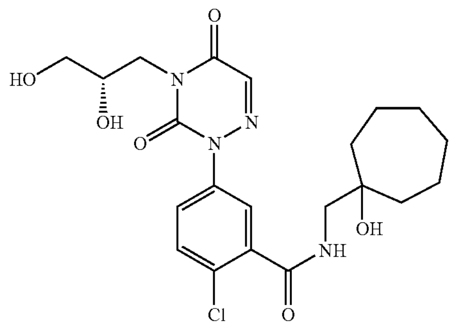 | 5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide |
| 42 | 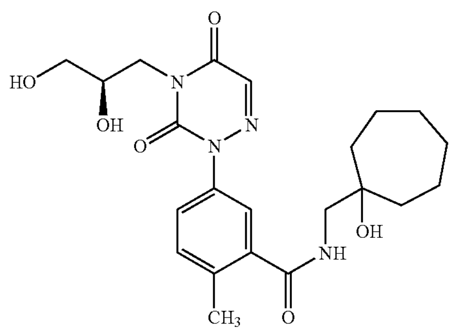 | 5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide |

II. In Vitro Evaluation of Compounds

The activity of the compounds of the invention for the various disorders described above can be determined according to one or more of the following assays. All of the compounds of the invention that were tested had an $IC_{50}$ of less than 10 µM in the in vitro assay described below.

Preferably, the compounds of the invention have an $IC_{50}$ in the in vitro assays described below of less than 100 nM, more preferably less than 50 nM, and most preferably less than 10 nM. Still further, the compounds of the invention preferably have an $IC_{50}$ in the range of 0.01 nM-100 nM, more preferably between 0.05 nM-50 nM, and most preferably between 0.10 nM-10 nM.

Pharmacological Analysis

Certain compounds such as benzoylbenzoyl adenosine triphosphate (bbATP) are known to be agonists of the $P2X_7$ receptor, effecting the formation of pores in the plasma membrane (Drug Development Research (1996), 37(3), p. 126). Consequently, when the receptor is activated using bbATP in the presence of ethidium bromide (a fluorescent DNA probe), an increase in the fluorescence of intracellular DNA-bound ethidium bromide is observed. Alternatively, the propidium dye YOPRO-1 can be substituted for ethidium bromide so as to detect uptake of the dye. The increase in fluorescence can be used as a measure of $P2X_7$ receptor activation and therefore to quantify the effect of a compound on the $P2X_7$ receptor.

In this manner, the compounds of the invention can be tested for antagonist activity at the $P2X_7$ receptor. 96-Well flat bottomed microtitre plates are filled with 250 µl of test solution comprising 200 µl of a suspension of THP-1 cells ($2.5 \times 10^6$ cells/ml, more preferably prestimulated as described in the literature with a combination of LPS and TNF to promote receptor expression) containing $10^{-4}$M ethidium bromide, 25 µl of a high potassium, low sodium buffer solution (10 mM Hepes, 150 mM KCl, 5 mM D-glucose and 1.0% FBS at pH 7.5) containing $10^{-5}$M bbATP, and 25 µl of the high potassium buffer solution containing $3 \times 10^{-5}$M test compound (more preferably $5 \times 10^{-4}$M, more preferably $1 \times 10^{-4}$M, more preferably $1 \times 10^{-3}$M). The plate is covered with a plastic sheet and incubated at 37° C. for one hour. The plate is then read in a Perkin-Elmer fluorescent plate reader, excitation 520 nm, emission 595 nm, slit widths: Ex 15 nm, Em 20 nm. For the purposes of comparison, bbATP (a $P2X_7$ receptor agonist) and pyridoxal 5-phosphate (a $P2X_7$ receptor antagonist) can be used separately in the test as controls. From the readings obtained, a $pIC_{50}$ figure can be calculated for each test compound, this figure being the negative logarithm of the concentration of test compound necessary to reduce the bbATP agonist activity by 50%. In like manner, the compounds of the invention can be tested for antagonist activity at the $P2X_7$ receptor using the cytokine IL-1β as the readout. Blood collected from normal volunteers in the presence of heparin is fractionated using lymphocyte separation medium obtained from Organon Technica (Westchester, Pa.). The region of the resulting gradient containing banded mononuclear cells is harvested, diluted with 10 ml of Maintenance Medium (RPMI 1640, 5% FBS, 25 mM Hepes, pH 7.2, 1% penicillin/streptomycin), and cells are collected by centrifugation. The resulting cell pellet was suspended in 10 ml of Maintenance Medium and a cell count was performed. In an average experiment, $2 \times 10^5$ mononuclear cells are seeded into each well of 96-well plates in a total volume of 0.1 ml. Monocytes are allowed to adhere for 2 hours, after which the supernatants are discarded and the attached cells are rinsed twice and then incubated in Maintenance Medium overnight at 37° C. in a 5% $CO_2$ environment. The cultured monocytes can be activated with 10 ng/ml LPS (*E. coli* serotype 055:B5; Sigma Chemicals, St. Louis, Mo.). Following a 2-hour incubation, the activation medium is removed, the cells are rinsed twice with 0.1 ml of Chase Medium (RPMI 1640, 1% FBS, 20 mM Hepes, 5 mM NaHCO$_3$, pH 6.9), and then 0.1 ml of Chase Medium containing a test agent is added and the plate is incubated for 30 minutes; each test agent concentration can be evaluated in triplicate wells. ATP then is introduced (from a 100 mM stock solution, pH 7) to achieve a final concentration of 2 mM and the plate is incubated at 37° C. for an additional 3 hours. Media were harvested and clarified by centrifugation, and their IL-1β content was determined by ELISA (R&D Systems; Minneapolis, Minn.).

III. Pharmaceutically Acceptable Salts and Solvates

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention (e.g., compounds of Formula I) are capable of further forming both pharmaceutically acceptable salts, including but not limited to acid addition and/or base salts. Pharmaceutically acceptable salts of the compounds of the present invention include the acid addition and base salts (including disalts) thereof. Examples of suitable salts can be found for example in Stahl and Wermuth, *Handbook of Pharmaceutical Salts: Properties, Selection, and Use*, Wiley-VCH, Weinheim, Germany (2002); and Berge et al., "Pharmaceutical Salts," *J. of Pharmaceutical Science*, 1977;66:1-19.

Pharmaceutically acceptable acid addition salts of the compounds of the present invention include non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include the acetate, aspartate, benzoate, besylate (benzenesulfonate), bicarbonate/carbonate, bisulfate, caprylate, camsylate (camphor sulfonate), chlorobenzoate, citrate, edisylate (1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of compounds of the present invention. Also contemplated are the salts of amino acids such as arginate, gluconate, galacturonate, and the like.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are aluminum, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

IV. Pharmaceutical Compositions and Methods of Administration

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use. The phrase "therapeutically effective amount" means an amount of a compound, or a pharmaceutically acceptable salt thereof, sufficient to inhibit, halt, or allow an improvement in the disease being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with a IL-1 mediated disorder as measured quantitatively or qualitatively.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a subject, in the context of the present invention should be sufficient to affect a beneficial therapeutic response in the subject over time. The term "subject" refers to a member of the class Mammalia. Examples of mammals include, without limitation, humans, primates, chimpanzees, rodents, mice, rats, rabbits, horses, livestock, dogs, cats, sheep, and cows.

The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject. Many different administration methods are known to those of skill in the art.

For administration, compounds of the present invention can be administered at a rate determined by factors that can include, but are not limited to, the pharmacokinetic profile of the compound, contraindicated drugs, and the side-effects of the compound at various concentrations, as applied to the mass and overall health of the subject. Administration can be accomplished via single or divided doses.

Examples of a typical tablet, parenteral, and patch formulation include the following:

TABLET FORMULATION EXAMPLE 1

| Tablet Formulation | |
|---|---|
| Ingredient | Amount |
| 2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide | 50 mg |

-continued

Tablet Formulation

| Ingredient | Amount |
| --- | --- |
| Lactose | 80 mg |
| Cornstarch (for mix) | 10 mg |
| Cornstarch (for paste) | 8 mg |
| Magnesium Stearate (1%) | 2 mg |
| | 150 mg |

2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide can be mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for treatment of an IL-1 mediated disease.

PARENTERAL SOLUTION FORMULATION
EXAMPLE 1

In a solution of 700 mL of propylene glycol and 200 mL of water for injection can be added 20.0 g of 2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide. The mixture is stirred, and the pH is adjusted to 5.5 with hydrochloric acid. The volume is adjusted to 1000 mL with water for injection. The solution is sterilized, filled into 5.0 mL ampules, each containing 2.0 mL (40 mg of invention compound), and sealed under nitrogen. The solution is administered by injection to a subject suffering from a IL-1 mediated disease and in need of treatment.

PATCH FORMULATION EXAMPLE 1

Ten milligrams of 2-Chloro-N-(1-hydroxy-cycloheptylmethyl)-5-[4-(2R-hydroxy-3-methoxy-propyl)-3,5-dioxo-4,5-dihydro-3H-[1,2,4]triazin-2-yl]-benzamide can be mixed with 1 mL of propylene glycol and 2 mg of acrylic-based polymer adhesive containing a resinous cross-linking agent. The mixture is applied to an impermeable backing (30 cm$^2$) and applied to the upper back of a patient for sustained release treatment of a IL-1 mediated disease (e.g., rheumatoid arthritis).

V. Methods for Treating IL-1 Mediated Diseases

The compounds of the present invention and pharmaceutical compositions comprising a compound of the present invention can be administered to a subject suffering from a IL-1 mediated disease. IL-1 mediated diseases can be treated prophylactically, acutely, and chronically using compounds of the present invention, depending on the nature of the disease. Typically, the host or subject in each of these methods is human, although other mammals can also benefit from the administration of a compound of the present invention.

In therapeutic applications, the compounds of the present invention can be prepared and administered in a wide variety of oral and parenteral dosage forms. The term "administering" refers to the method of contacting a compound with a subject. Thus, the compounds of the present invention can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of the present invention can be administered transdermally, topically, via implantation, transdermally, topically, and via implantation. In certain embodiments, the compounds of the present invention are delivered orally. The compounds can also be delivered rectally, bucally, intravaginally, ocularly, andially, or by insufflation.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired. The term "treatment" includes the acute, chronic, or prophylactic diminishment or alleviation of at least one symptom or characteristic associated with or caused by the disorder being treated. For example, treatment can include diminishment of several symptoms of a disorder, inhibition of the pathological progression of a disorder, or complete eradication of a disorder. The compounds of the present invention can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times. For example, a subject that is administered a first dosage that comprises a compound of the present invention at 8 a.m. and then is administered a second therapeutic agent at 1-12 hours later, e.g., 6 p.m., of that same day has been co-administered with a compound of the present invention and the second therapeutic agent. Alternatively, for example, a subject could be administered with a single dosage comprising a compound of the present invention and a second therapeutic agent at 8 a.m. has been co-administered with a compound of the present invention and the second therapeutic agent.

Thus, compounds of the invention can also be co-administered with compounds that are useful for the treatment of cancer (e.g., cytotoxic drugs such as TAXOL®, taxotere, GLEEVEC® (Imatinib Mesylate), adriamycin, daunomycin, cisplatin, etoposide, a vinca alkaloid, vinblastine, vincristine, methotrexate, or adriamycin, daunomycin, cis-platinum, etoposide, and alkaloids, such as vincristine, farnesyl transferase inhibitors, endostatin and angiostatin, VEGF inhibitors, and antimetabolites such as methotrexate. The compounds of the present invention may also be used in combination with a taxane derivative, a platinum coordination complex, a nucleoside analog, an anthracycline, a topoisomerase inhibitor, or an aromatase inhibitor). Radiation treatments can also be co-administered with a compound of the present invention for the treatment of cancers.

The compounds of the invention can also be co-administered with compounds that are useful for the treatment of a thrombolytic disease, heart disease, stroke, etc., (e.g., aspirin, streptokinase, tissue plasminogen activator, urokinase, anticoagulants, antiplatelet drugs (e.g., PLAVIX®; clopidogrel bisulfate), a statin (e.g., LIPITOR(D (Atorvastatin calcium), ZOCOR® (Simvastatin), CRESTOR® (Rosuvastatin), etc.), a Beta blocker (e.g, Atenolol), NORVASC® (amlodipine besylate), and an ACE inhibitor (e.g., Accupril® (Quinapril Hydrochloride), Lisinopril, etc.).

The compounds of the invention can also be co-administered for the treatment of hypertension with compounds such as ACE inhibitors, lipid lowering agents such as statins, LIPITOR® (Atorvastatin calcium), calcium channel blockers such as NORVASC® (amlodipine besylate). The compounds of the present invention may also be used in combination with fibrates, beta-blockers, NEPI inhibitors, Angiotensin-2 receptor antagonists and platelet aggregation inhibitors.

For the treatment of inflammatory diseases, including rheumatoid arthritis, the compounds of the invention may be co-administered with agents such as TNF-α inhibitors such as anti-TNFα monoclonal antibodies (such as REMICADE®, CDP-870 and HUMIRA™ (adalimumab) and TNF receptor-immunoglobulin fusion molecules (such as ENBREL®), IL-1 inhibitors, receptor antagonists or soluble IL-1Rα (e.g. KINERET™ or ICE inhibitors), nonsteroidal anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin,COX-2 inhibitors (such as CELEBREX® (celecoxib), VIOXX® (rofecoxib), BEXTRA®D (valdecoxib) and etoricoxib, metalloprotease inhibitors (preferably MMP-13 selective inhibitors), NEUROTIN®, pregabalin, low dose methotrexate, sulfasalazine, leflunomide, hydroxychloroquine, d-penicillamine, auranofin or parenteral or oral gold.

The compounds of the invention may be co-administered with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the invention may also be co-administered with antiviral agents such as Viracept, AZT, aciclovir and famciclovir, and antisepsis compounds such as Valant.

The compounds of the present invention may further be co-administered with CNS agents such as antidepressants (such as sertraline), anti-Parkinsonian drugs (such as deprenyl, L-Dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), NEURONTIN®, pregabalin, and anti-Alzheimer's drugs such as ARICEPT®, tacrine, propentofylline or metrifonate.

The compounds of the present invention may additionally be co-administered with osteoporosis agents such as EVISTA® (raloxifene hydrochloride), droloxifene, lasofoxifene, or FOSAMAX® and immunosuppressant agents such as FK-506 and rapamycin.

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of formula X:

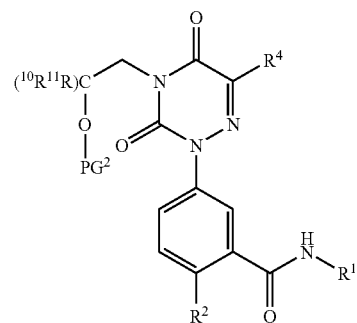

wherein R1 is (C1-C6)alkyl, optionally substituted by (C3-C8)cycloalkyl, phenyl, naphthyl, a 5 or 6-membered heterocycloalkyl, or a 5- or 6-membered heteroaryl, wherein each of said (C1-C6)alkyl, (C3-C8)cycloalkyl, phenyl, naphthyl, a 5 or 6-membered heterocycloalkyl, or 5- or 6-membered heteroaryl are optionally substituted by one to three moieties independently selected from the group consisting of hydroxy, halo, —CN, (C1-C6)alkyl, —(C1-C6)alkyl-OH, (C1-C6)alkyl-NH(C=O)—, NH2(C=O)—, (C1-C6) alkoxy, and (C3-C8)cycloalkyl;

$R^2$ is hydrogen, halo, —CN, or $(C_1-C_6)$alkyl, wherein said $(C_1-C_6)$alkyl is optionally substituted by one to three moieties, independently selected from the group consisting of halo, hydroxy, amino, —CN, $(C_1-C_6)$alkyl, $(C_1-C_6)$alkoxy, —CF$_3$, CF$_3$O—, $(C_1-C_6)$alkyl-NH—, [$(C_1-C_6)$alkyl]$_2$—N—, $(C_1-C_6)$alkyl-S—, $(C_1-C_6)$ alkyl-(S=O)—, $(C_1-C_6)$alkyl-(SO$_2$)—, $(C_1-C_6)$alkyl-O—(C=O)—, formyl, $(C_1-C_6)$alkyl-(C=O)—, and $(C_3-C_6)$cycloalkyl;

wherein $R^4$ is independently selected from the group consisting of hydrogen, halo, hydroxy, —CN, HO—$(C_1-C_6)$alkyl, $(C_1-C_6)$alkyl optionally substituted with one to three fluoro, $(C_1-C_6)$alkoxy optionally substituted with one to three fluoro, —CO$_2$H, $(C_1-C_6)$alkyl-O—(C=O)—, $R^5R^6N(O_2S)$—, $(C_1-C_6)$alkyl-(O$_2$S)—NH—, $(C_1-C_6)$alkyl-O$_2$S—[$(C_1-C_6)$alkyl-N]—, $R^5R^6N(C=O)$—, $R^5R^6N(CH_2)_m$—, phenyl, naphthyl, $(C_3-C_8)$cycloalkyl, a 5- or 6-membered heteroaryl, a 5 or 6-membered heterocycloalkyl, phenyl-O—, naphthyl-O—, $(C_3-C_8)$cycloalkyl-O—, a 5- or 6-membered heteroaryloxy and 5 or 6-membered heterocycloalkyl-O—;

PG$^2$ is selected from the group consisting of: trimethylsilyl, triethylsilyl, tri-isopropylsilyl, dimethylisopropylsilyl, diethylisopropylsilyl diethylisopropylsilyl, dimethylthexylsilyl, tert-butyldimethylsilyl, di-tert-butylmethylsilyl, tert-butyldiphenylsilyl, tribenzylsilyl, tri-p-xylylsilyl, triphenylsilyl, diphenylmethylsilyl, and tert-butyl(methoxy)diphenylsilyl;

$R^5$ and $R^6$ are each independently selected from the group consisting of hydrogen, $(C_1\text{-}C_6)$alkyl, —$(C_2\text{-}C_6)$alkyl-OH, and $(C_3\text{-}C_8)$cycloalkyl, or $R^5$ and $R^6$ may optionally be taken together with the nitrogen atom to which they are attached to form a 5 or 6-membered heterocycloalkyl;

$R^{10}$ and $R^{11}$ are independently selected from the group consisting of: $(C_1\text{-}C_6)$alkyl optionally substituted with one to three halos, hydroxy, —CN, $(C_1\text{-}C_6)$alkoxy-, $((C_1\text{-}C_6)\text{alkyl})_2$—N—, $(C_1\text{-}C_6)$alkyl-(C=O)—, $(C_3\text{-}C_8)$cycloalkyl-(C=O)—, a 5 or 6-membered heterocycloalkyl-(C=O)—, phenyl-(C=O)—, naphthyl-(C=O)—, a 5- or 6-membered heteroaryl-(C=O)—, $(C_1\text{-}C_6)$alkyl-(C=O)O—, $(C_1\text{-}C_6)$alkyl-O(C=O)—, $(C_3\text{-}C_8)$cycloalkyl, phenyl, naphthyl, a 5 or 6-membered heterocycloalkyl, and 5- or 6-membered heteroaryl; and m is one or two.

2. The compound of claim 1 wherein said compound of formula X is 5-{4-[2-(tert-butyl-dimethyl-silanyloxy)-3-methoxy-propyl]-3,5-dioxo-4,5-dihydro-3H-[1,2,4]triazin-2-yl}-2-chloro-N-(1-hydroxy-cycloheptylmethyl)-benzamide.

3. The compound of claim 1 wherein R1 is a (C1-C4) alkyl, optionally substituted by (C3-C8)cycloalkyl; wherein said (C1-C4)alkyl or (C3-C8)cycloalkyl are optionally substituted by one to three moieties independently selected from the group consisting of hydroxy, halo, —CN, (C1-C6)alkyl, —(C1-C6)alkyl-OH, (C1-C6)alkyl-NH(C=O)—, NH2(C=O)—, (C1-C6)alkoxy, and (C3-C8)cycloalkyl.

4. The compound of claim 1 wherein R2 is chloro, methyl or ethyl.

5. The compound of claim 1 wherein R4 is hydrogen and R10 and R11 are independently selected from the group consisting of: hydrogen and (C1-C6)alkyl optionally substituted with (C1-C6)alkoxy- or —OH.

* * * * *